United States Patent
Fukuda

(10) Patent No.: US 11,010,937 B2
(45) Date of Patent: May 18, 2021

(54) IMAGE PROCESSING APPARATUS, IMAGE PROCESSING METHOD, AND IMAGE PROCESSING PROGRAM

(71) Applicant: FUJIFILM Corporation, Tokyo (JP)

(72) Inventor: Wataru Fukuda, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 101 days.

(21) Appl. No.: 16/210,901

(22) Filed: Dec. 5, 2018

(65) Prior Publication Data
US 2019/0221010 A1 Jul. 18, 2019

(30) Foreign Application Priority Data
Jan. 17, 2018 (JP) .............................. JP2018-005704

(51) Int. Cl.
*G06T 11/00* (2006.01)
*A61B 6/02* (2006.01)
(Continued)

(52) U.S. Cl.
CPC ............ *G06T 11/006* (2013.01); *A61B 6/025* (2013.01); *A61B 6/032* (2013.01); *A61B 6/4452* (2013.01);
(Continued)

(58) Field of Classification Search
CPC ......... G06T 11/006; G06T 2207/10081; G06T 2207/10112; A61B 6/025; A61B 6/032;
(Continued)

(56) References Cited

U.S. PATENT DOCUMENTS 6,512,854 B1 * 1/2003 Mucci ..................... G06T 5/002
382/128
10,043,294 B2 8/2018 Fukuda
(Continued)

FOREIGN PATENT DOCUMENTS

JP 2015-86344 A 4/2015
JP 5952251 B2 7/2016
(Continued)

OTHER PUBLICATIONS

Japanese Office Action for corresponding Japanese Application No. 2018-005704, dated Feb. 9, 2021, with English translation.

*Primary Examiner* — Zhitong Chen
(74) *Attorney, Agent, or Firm* — Birch, Stewart, Kolasch & Birch, LLP

(57) ABSTRACT

Provided are an image processing apparatus, an image processing method, and a non-transitory recording medium storing an image processing program that can further improve the quality of a pseudo two-dimensional image generated using tomographic images. A control unit of a console acquires a plurality of projection images obtained by irradiating a subject disposed between a radiation source and a radiation detector with radiation emitted from the radiation source at different irradiation angles and capturing the radiation with the radiation detector at each of the irradiation angles. In addition, the control unit generates a pseudo two-dimensional image by reducing a weight of a noise pixel which is more affected by noise than a pixel of an object of interest or excluding the noise pixel, using a plurality of tomographic images reconstructed from the plurality of projection images.

18 Claims, 16 Drawing Sheets

(51) Int. Cl.
 *A61B 6/03* (2006.01)
 *A61B 6/00* (2006.01)
(52) U.S. Cl.
 CPC .......... *A61B 6/5235* (2013.01); *A61B 6/5258* (2013.01); *G06T 2207/10081* (2013.01); *G06T 2207/10112* (2013.01)
(58) Field of Classification Search
 CPC .... A61B 6/4452; A61B 6/5235; A61B 6/5258
 See application file for complete search history.

(56) References Cited

U.S. PATENT DOCUMENTS

| | | | | |
|---|---|---|---|---|
| 2005/0226484 | A1* | 10/2005 | Basu | G06T 11/005 382/131 |
| 2015/0302615 | A1* | 10/2015 | Fukuda | G06T 11/006 378/19 |
| 2016/0095563 | A1* | 4/2016 | Fukuda | G06T 7/97 378/21 |
| 2016/0206268 | A1 | 7/2016 | Fukuda | |
| 2017/0071554 | A1 | 3/2017 | Fukuda | |
| 2017/0316588 | A1 | 11/2017 | Homann et al. | |

FOREIGN PATENT DOCUMENTS

| | | |
|---|---|---|
| JP | 2017-55973 A | 3/2017 |
| JP | 2017-535344 A | 11/2017 |

\* cited by examiner

IMAGE PROCESSING APPARATUS, IMAGE PROCESSING METHOD, AND IMAGE PROCESSING PROGRAM

CROSS-REFERENCE TO RELATED APPLICATIONS

The present application claims priority under 35 U.S.C. § 119 to Japanese Patent Application No. 2018-005704, filed on Jan. 17, 2018. Each of the above application is hereby expressly incorporated by reference, in its entirety, into the present application.

BACKGROUND OF THE INVENTION

1. Field of the Invention

The present disclosure relates to an image processing apparatus, an image processing method, and a non-transitory recording medium storing an image processing program.

2. Description of the Related Art

As a radiography method, so-called tomosynthesis imaging has been known which sequentially emits radiation from each of a plurality of irradiation positions with different irradiation angles and captures a plurality of projection images at each irradiation position using a radiation detector. In addition, a technique has been known which generates a tomographic image from a plurality of projection images obtained by tomosynthesis imaging, using a reconstruction process.

Further, a technique has been known which generates a pseudo two-dimensional image corresponding to a two-dimensional image captured by emitting radiation from a radiation source located at a fixed irradiation position, using a plurality of tomographic images having different distances from a detection surface of a radiation detector to a radiation source (a position in a height direction) (see JP5952251B).

SUMMARY OF THE INVENTION

However, in the tomosynthesis imaging, the angle at which radiation is emitted is limited. Therefore, in a case in which a plurality of projection images are superimposed to reconstruct tomographic images, an artifact, such as a ripple artifact indicating a virtual image (residual image) of an object included in a region in which no objects are originally present, is likely to be generated.

In a case in which a pseudo two-dimensional image is generated using tomographic images including artifacts, the quality of the generated pseudo two-dimensional image is degraded by the influence of the artifacts.

JP5952251B discloses a technique that reduces the artifacts caused by the residual image in the tomographic image. However, there is room for improvement in the quality of a pseudo two-dimensional image.

The present disclosure has been made in view of the above-mentioned problem and an object of the present disclosure is to provide an image processing apparatus, an image processing method, and an image processing program that can further improve the quality of a pseudo two-dimensional image generated using tomographic images.

In order to achieve the object, according to a first aspect of the present disclosure, there is a provided an image processing apparatus comprising: an acquisition unit that acquires a plurality of projection images obtained by irradiating a subject disposed between a radiation source and a radiation detector with radiation emitted from the radiation source at different irradiation angles and capturing the radiation with the radiation detector at each of the irradiation angles; and a generation unit that generates a pseudo two-dimensional image by reducing a weight of a noise pixel which is more affected by noise than a pixel of an object of interest or excluding the noise pixel, using a plurality of tomographic images reconstructed from the plurality of projection images.

According to a second aspect of the present disclosure, in the image processing apparatus according to the first aspect, the noise pixel may be a pixel having a value whose difference from a mean of values of corresponding pixels on a specific projection path in the plurality of tomographic images is equal to or less than a predetermined threshold value.

According to a third aspect of the present disclosure, in the image processing apparatus according to the first aspect, the noise pixel may be a pixel of interest included in at least one region of interest that is selected from the regions of interest including corresponding pixels of interest on a specific path in the plurality of tomographic images in ascending order of a variance of the values of the pixels included in the region of interest.

According to a fourth aspect of the present disclosure, in the image processing apparatus according to any one of the first to third aspects, in a case in which a plurality of noise pixels are present on the projection path, the generation unit may reduce the weights of some of the noise pixels or exclude some of the noise pixels.

According to a fifth aspect of the present disclosure, in the image processing apparatus according to the fourth aspect, a ratio of the number of some noise pixels to the number of tomographic images may be equal to or less than a predetermined value.

According to a sixth aspect of the present disclosure, the image processing apparatus according to any one of the first to fifth aspects may further comprise: a decomposition unit that decomposes each of the plurality of projection images into a plurality of first projection images with a low-frequency component lower than a predetermined spatial frequency and a plurality of second projection images with a high-frequency component higher than the predetermined spatial frequency. The generation unit may generate a pseudo two-dimensional image by reducing the weight of the noise pixel which is more affected by noise than the pixel of the object of interest or excluding the noise pixel in each of a plurality of second tomographic images reconstructed from the plurality of second projection images, using a plurality of first tomographic images reconstructed from the plurality of first projection images and the plurality of second tomographic images.

According to a seventh aspect of the present disclosure, in the image processing apparatus according to the sixth aspect, the generation unit may perform a process for preventing an influence of a residual image for the plurality of first projection images to reconstruct the plurality of first projection images into the plurality of first tomographic images.

According to an eighth aspect of the present disclosure, in the image processing apparatus according to the sixth or seventh aspect, the generation unit may give a smaller weight to the plurality of first projection images as the irradiation angle becomes larger to reconstruct the plurality of first projection images into the plurality of first tomographic images.

According to a ninth aspect of the present disclosure, in the image processing apparatus according to any one of the sixth to eighth aspects, the generation unit may generate a first pseudo two-dimensional image using the plurality of first tomographic images, generate a second pseudo two-dimensional image using the plurality of second tomographic images, and combine the first pseudo two-dimensional image and the second pseudo two-dimensional image to generate a composite pseudo two-dimensional image as the pseudo two-dimensional image.

According to a tenth aspect of the present disclosure, in the image processing apparatus according to any one of the sixth to eighth aspects, the generation unit may combine each of the plurality of first tomographic images and each of the plurality of second tomographic images for each height according to the height based on a detection surface of the radiation detector to generate a plurality of composite tomographic images and generate a composite pseudo two-dimensional image as the pseudo two-dimensional image, using the plurality of composite tomographic images.

In order to achieve the object, according to an eleventh aspect of the present disclosure, there is provided an image processing method comprising: acquiring a plurality of projection images obtained by irradiating a subject disposed between a radiation source and a radiation detector with radiation emitted from the radiation source at different irradiation angles and capturing the radiation with the radiation detector at each of the irradiation angles; and generating a pseudo two-dimensional image by reducing a weight of a noise pixel which is more affected by noise than a pixel of an object of interest or excluding the noise pixel, using a plurality of tomographic images reconstructed from the plurality of projection images.

In order to achieve the object, according to a twelfth aspect of the present disclosure, there is provided a non-transitory recording medium storing an image processing program that causes a computer to perform: acquiring a plurality of projection images obtained by irradiating a subject disposed between a radiation source and a radiation detector with radiation emitted from the radiation source at different irradiation angles and capturing the radiation with the radiation detector at each of the irradiation angles; and generating a pseudo two-dimensional image by reducing a weight of a noise pixel which is more affected by noise than a pixel of an object of interest or excluding the noise pixel, using a plurality of tomographic images reconstructed from the plurality of projection images.

According to the present disclosure, it is possible to further improve the quality of a pseudo two-dimensional image generated using tomographic images.

DESCRIPTION OF THE PREFERRED EMBODIMENTS

Hereinafter, embodiments of the invention will be described in detail with reference to the drawings. These embodiments do not limit the invention.

First Embodiment

Figure 1:
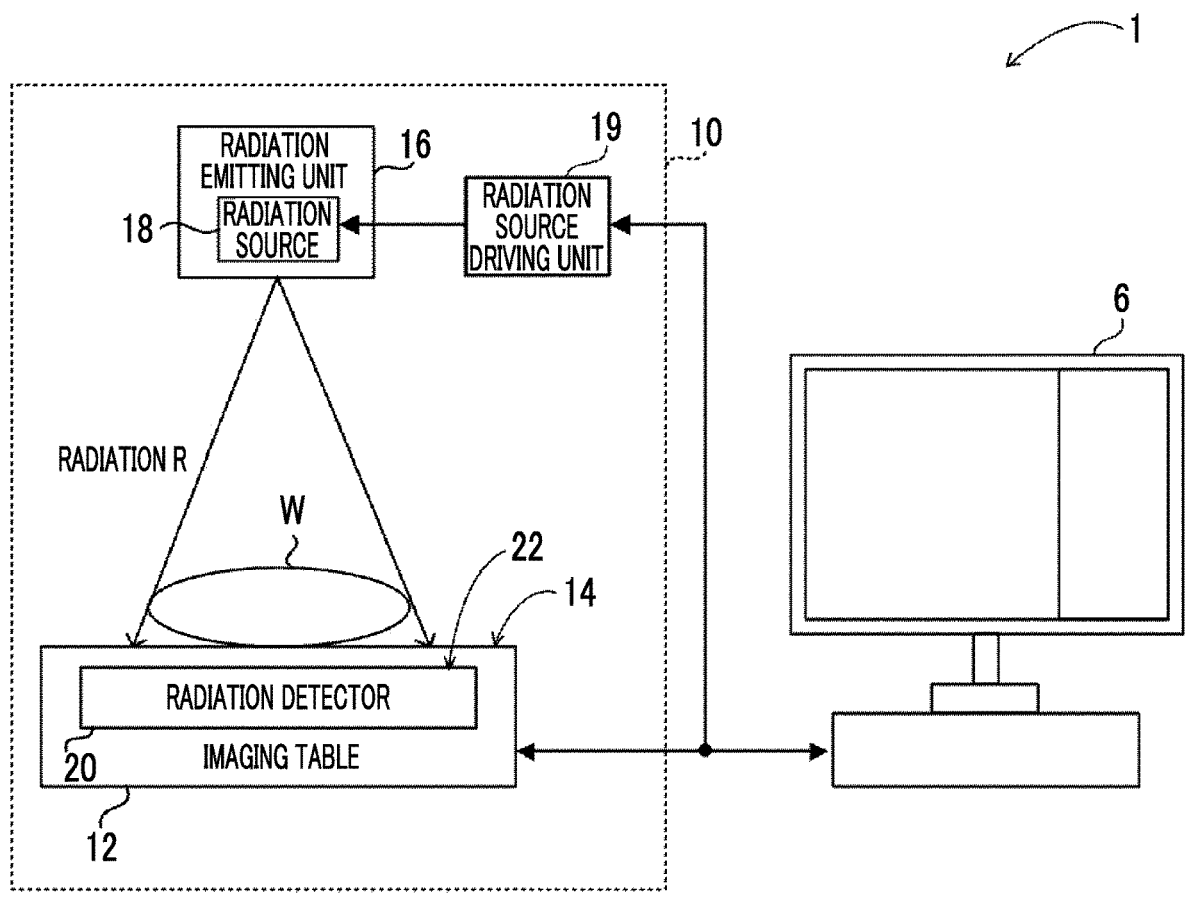
FIG. 1 is a diagram illustrating an example of the overall configuration of a radiography system according to a first embodiment.
Figure 2:
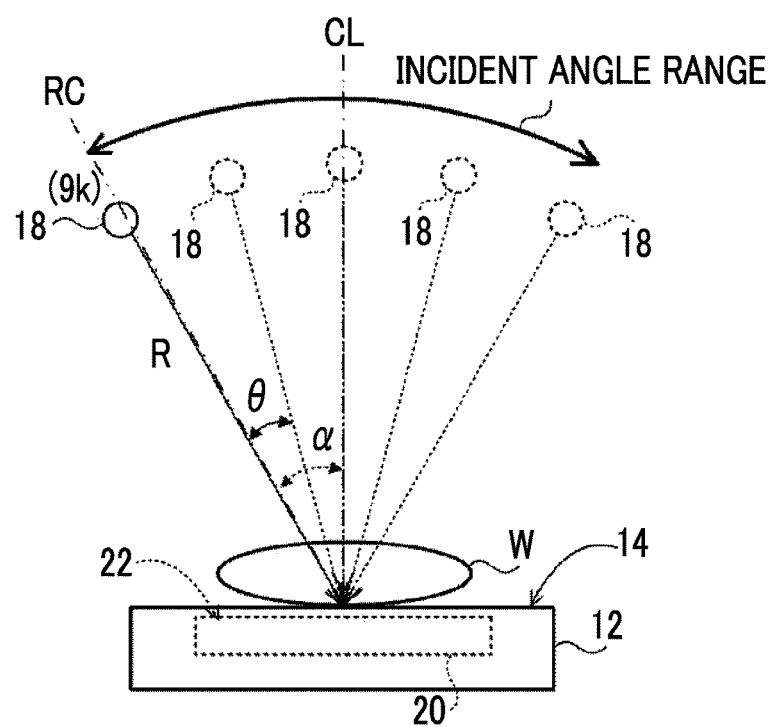
FIG. 2 is a diagram illustrating tomosynthesis imaging performed by a radiography apparatus according to the first embodiment.

First, an example of the overall configuration of a radiography system according to this embodiment will be described. FIG. 1 is a diagram illustrating an example of the overall configuration of a radiography system 1 according to this embodiment. In addition, FIG. 2 is a diagram illustrating tomosynthesis imaging (which will be described in detail below) by a radiography apparatus 10 according to this embodiment.

As illustrated in FIG. 1, the radiography system 1 according to this embodiment comprises a console 6 and the radiography apparatus 10. In the radiography system 1 according to this embodiment, the radiography apparatus 10 captures a radiographic image of a subject W on the basis of a command (imaging order) input from an external system (for example, a radiology information system (RIS)) through the console 6 in response to the operation of a user such as a doctor or a radiology technician.

Figure 3:
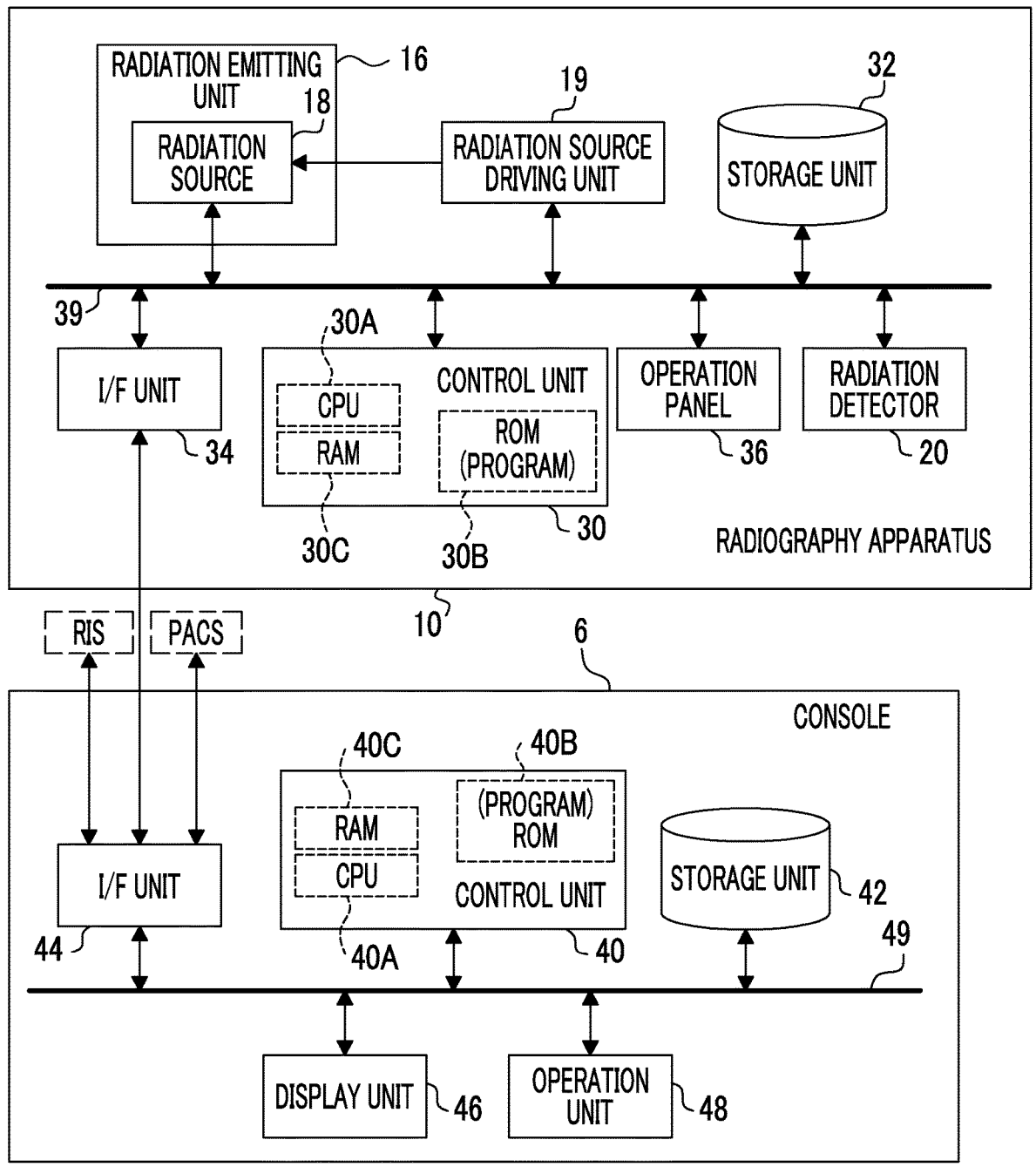
FIG. 3 is a block diagram illustrating an example of the configuration of a console and the radiography apparatus according to the first embodiment.

FIG. 3 is a block diagram illustrating an example of the configuration of the console 6 and the radiography apparatus 10 according to this embodiment. Hereinafter, the console 6 and the radiography apparatus 10 according to this embodiment will be described with reference to FIGS. 1 to 3. The console 6 according to this embodiment is an example of an image processing apparatus according to the present disclosure.

The radiography apparatus 10 according to this embodiment is an apparatus that irradiates the subject W with radiation R (for example, X-rays) and captures the radiographic image of the subject W. In addition, the radiography apparatus 10 according to this embodiment has a function of performing so-called tomosynthesis imaging (which will be described in detail below) and simple imaging.

A radiation detector 20 that detects the radiation R transmitted through the subject W and an imaging surface 14 of an imaging table 12 is provided in the imaging table 12. The radiography apparatus 10 generates a radiographic image on the basis of the radiation R detected by the radiation detector 20. However, the type of radiation detector 20 is not particularly limited. For example, the radiation detector 20 may be an indirect-conversion-type radiation detector that converts the radiation R into light and converts the converted light into charge or a direct-conversion-type radiation detector that directly converts the radiation R into charge. In this embodiment, image data indicating the radiographic image output from the radiation detector 20 of the radiography apparatus 10 is transmitted to the console 6.

A radiation source 18 provided in a radiation emitting unit 16 of the radiography apparatus 10 is supported while being separated from the imaging surface 14 of the imaging table 12, that is, a detection surface 22 of the radiation detector 20 by a predetermined distance.

In a case in which the radiography apparatus 10 performs the tomosynthesis imaging, a radiation source driving unit 19 continuously moves the radiation source 18 of the radiation emitting unit 16 to each of a plurality of irradiation positions with different irradiation angles. In this embodiment, as illustrated in FIG. 2, the radiation source 18 is moved to irradiation positions 9k (k=0, 1, K; in FIG. 2, K=5) with different irradiation angles which are spaced a predetermined angle θ apart, that is, the positions where the incident angles of the radiation R with respect to the detection surface 22 of the radiation detector 20 are different from each other. At each irradiation position, the radiation source 18 emits the radiation R in response to a command from the console 6 and the radiation detector 20 captures a radiographic image. Hereinafter, in the tomosynthesis imaging, the radiographic images captured by the radiation detector 20 at a plurality of irradiation positions with different irradiation angles are referred to as "projection images". In a case in which the radiography system 1 performs the tomosynthesis imaging in which the radiation source 18 is moved to each of the irradiation positions 9k and the projection images are captured at each irradiation position 9k, K projection images are obtained.

As illustrated in FIG. 2, the incident angle of the radiation R means an angle α formed between a line CL normal to the detection surface 22 of the radiation detector 20 and a radiation axis RC. Here, the detection surface 22 of the radiation detector 20 is substantially parallel to the imaging surface 14. Hereinafter, a predetermined range in which the incident angles are different from each other in the tomosynthesis imaging as illustrated in FIG. 2 is referred to as an "incident angle range". An example of the incident angle range is a range of ±10 degrees or ±20 degrees with respect to the line CL normal to the detection surface 22 of the radiation detector 20. In this embodiment, for the radiation R, the "incident angle" is synonymous with the "irradiation angle".

In contrast, in a case in which the radiography apparatus 10 performs the simple imaging, the radiation source 18 of the radiation emitting unit 16 is at an irradiation position (an irradiation position along a normal direction) where the irradiation angle α is 0 degrees. The radiation source 18 emits the radiation R in response to a command from the console 6 and the radiation detector 20 captures a radiographic image. Hereinafter, the radiographic image captured by the radiation detector 20 in the simple imaging is referred to as a "two-dimensional image".

In addition, as illustrated in FIG. 3, the radiography apparatus 10 according to this embodiment comprises the radiation detector 20, the radiation emitting unit 16, the radiation source driving unit 19, a control unit 30, a storage unit 32, an interface (I/F) unit 34, and an operation panel 36. The radiation detector 20, the radiation source 18, the control unit 30, the storage unit 32, the I/F unit 34, the operation panel 36, and the radiation source driving unit 19 are connected to each other through a bus 39 such as a system bus or a control bus.

The control unit 30 according to this embodiment comprises a central processing unit (CPU) 30A, a read only memory (ROM) 30B, and a random access memory (RAM) 30C. The CPU 30A controls the overall operation of the radiography apparatus 10 in response to a command from the console 6. For example, various programs including an image processing program (which will be described below) executed by the CPU 30A are stored in the ROM 30B in advance. The RAM 30C temporarily stores various kinds of data.

For example, the image data of the radiographic image captured by the radiation detector 20 and various other kinds of information are stored in the storage unit 32. Examples of the storage unit 32 include a hard disk drive (HDD) and a solid state drive (SSD). The I/F unit 34 transmits and receives various kinds of information to and from the console 6 using at least one of wireless communication or wired communication. For example, the operation panel 36 is provided as a plurality of switches in the imaging table 12 of the radiography apparatus 10. In addition, the operation panel 36 may be provided as a touch panel.

In contrast, the console 6 according to this embodiment controls the radiography apparatus 10, using, for example, an imaging order or various other kinds of information acquired from an external system, such as an RIS, through a wireless communication local area network (LAN). In addition, the console 6 according to this embodiment can generate a tomographic image which will be described in detail below and a pseudo two-dimensional image (which will be described in detail below) from the projection images.

As illustrated in FIG. 3, the console 6 according to this embodiment comprises a control unit 40, a storage unit 42, an I/F unit 44, a display unit 46, and an operation unit 48. The control unit 40, the storage unit 42, the I/F unit 44, the display unit 46, and the operation unit 48 are connected to each other through a bus 49 such as a system bus or a control bus.

The control unit 40 according to this embodiment controls the overall operation of the console 6. The control unit 40 according to this embodiment comprises a CPU 40A, a ROM 40B, and a RAM 40C. The CPU 40A controls the overall operation of the console 6. For example, various programs including an image processing program (which will be described below) executed by the CPU 40A are stored in the ROM 40B in advance. The RAM 40C temporarily stores various kinds of data. The CPU 40A according to this embodiment executes the image processing program such that the control unit 40 functions as an example of an acquisition unit and a generation unit according to the present disclosure.

For example, the image data of the radiographic image captured by the radiography apparatus 10 and various other kinds of information are stored in the storage unit 42. Examples of the storage unit 42 include an HDD and an SSD.

The I/F unit 44 transmits and receives various kinds of information to and from the radiography apparatus 10 or external systems, such as an RIS and a picture archiving and communication system (PACS), using at least one of wireless communication or wired communication.

The display unit 46 displays, for example, information related to imaging and the captured radiographic images. The operation unit 48 is used by a user to input, for example, a command to capture a radiographic image and a command related to image processing on the captured radiographic image. For example, the operation unit 48 may have the form of a keyboard or the form of a touch panel integrated with the display unit 46.

Next, the operation of the console 6 in the radiography system 1 according to this embodiment will be described. As described above, the console 6 according to this embodiment can generate a tomographic image from a series of projection images captured by the tomosynthesis imaging. In addition, in this embodiment, the "tomographic image" is a radiographic image indicating the cross section (tomographic plane) of the subject W at a certain height in a height direction based on the detection surface 22 of the radiation detector 20. In addition, in this embodiment, the "height" means a distance from the detection surface 22 of the radiation detector 20 to the radiation source 18.

Furthermore, the console 6 according to this embodiment can generate, as a pseudo two-dimensional image, a pseudo two-dimensional image corresponding to a two-dimensional image captured by emitting the radiation R from the irradiation position (the irradiation position along the normal direction) where the irradiation angle α is 0 degrees, using a series of tomographic images in which the positions of the subject W in the height direction are different from each other. An example of the series of tomographic images is a plurality of tomographic images corresponding to the overall height (thickness) of the subject W.

Figure 4:
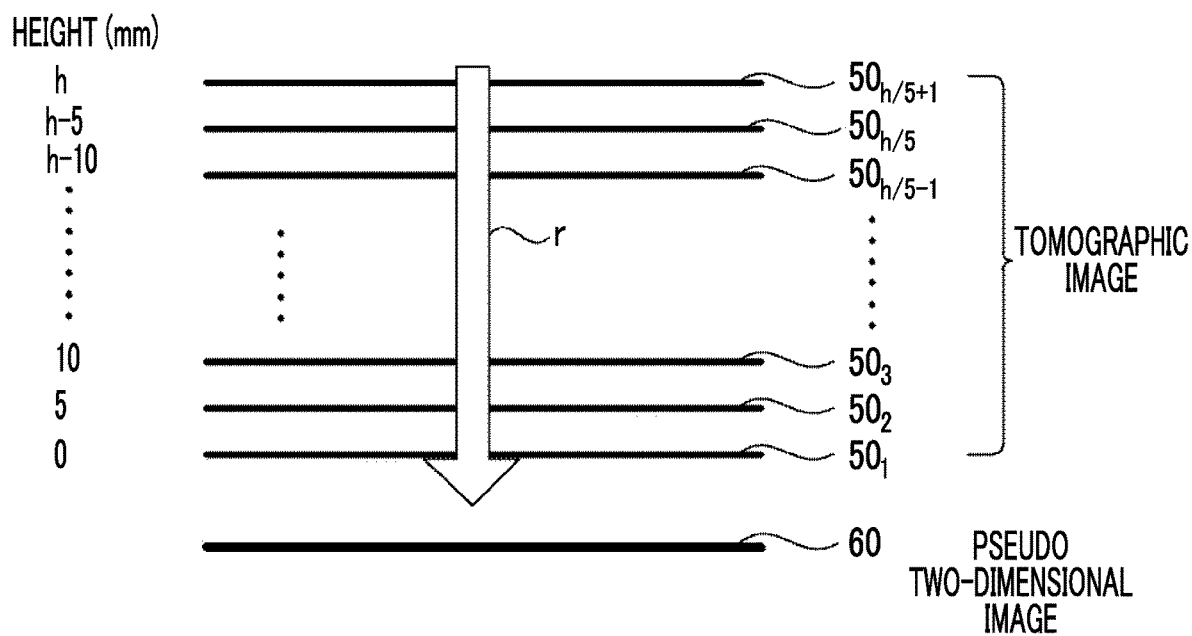
FIG. 4 is a diagram illustrating the generation of a pseudo two-dimensional image using tomographic images.

For example, in a case in which the console 6 generates the tomographic images of the subject W with an overall height of h (mm) at an interval of 5 (mm), h/5+1 tomographic images, that is, tomographic images $50_1$ to $50_{h/5+1}$ are generated as illustrated in FIG. 4. In this case, the console 6 can generate a pseudo two-dimensional image 60 using the tomographic images $50_1$ to $50_{h/5+1}$ in a projection path along a projection direction r represented by an arrow illustrated in FIG. 4. The projection path along the projection direction r in this embodiment is an example of a specific projection path according to the present disclosure.

Hereinafter, in a case in which various radiographic images, such as a projection image, a two-dimensional image, a tomographic image, and a pseudo two-dimensional image, are generically referred to without being distinguished from each other, they are simply referred to as "radiographic images".

In general, the pseudo two-dimensional image tends to have a lower image quality than the two-dimensional image obtained by the simple imaging. For example, the quality of the pseudo two-dimensional image is degraded by signal degradation that occurs in the generation of the pseudo two-dimensional image. The signal degradation will be described with reference to FIGS. 5 and 6. In general, an image (pixel) including an object of interest tends to be present in some tomographic images among a series of tomographic images. For example, in the example illustrated in FIG. 5, a pixel 70 of the object of interest is present in a tomographic image $51_4$ among the tomographic images $51_1$ to $51_7$ and is not present in the other tomographic images $51_1$ to $51_3$ and $51_5$ to $51_7$. In contrast, noise that is normally generated, such as quantum noise or white noise, is present in all of the tomographic images $51_1$ to $51_7$. Here, in a case in which the number T of tomographic images (T=7 in FIG. 5) is averaged, the amount of noise superimposed on one tomographic image is $1/\sqrt{T}$ and the intensity of the signal is 1/T. Therefore, as the number of tomographic images becomes larger, the signal-to-noise (SN) ratio becomes lower at $1/\sqrt{T}$ as illustrated in FIG. 6.

Therefore, in a case in which a pseudo two-dimensional image is generated, the console 6 according to this embodiment determines whether the influence of noise on each pixel of the tomographic image reconstructed from the projection image is large in image processing in order to prevent signal degradation (which will be described in detail below).

Figure 7:
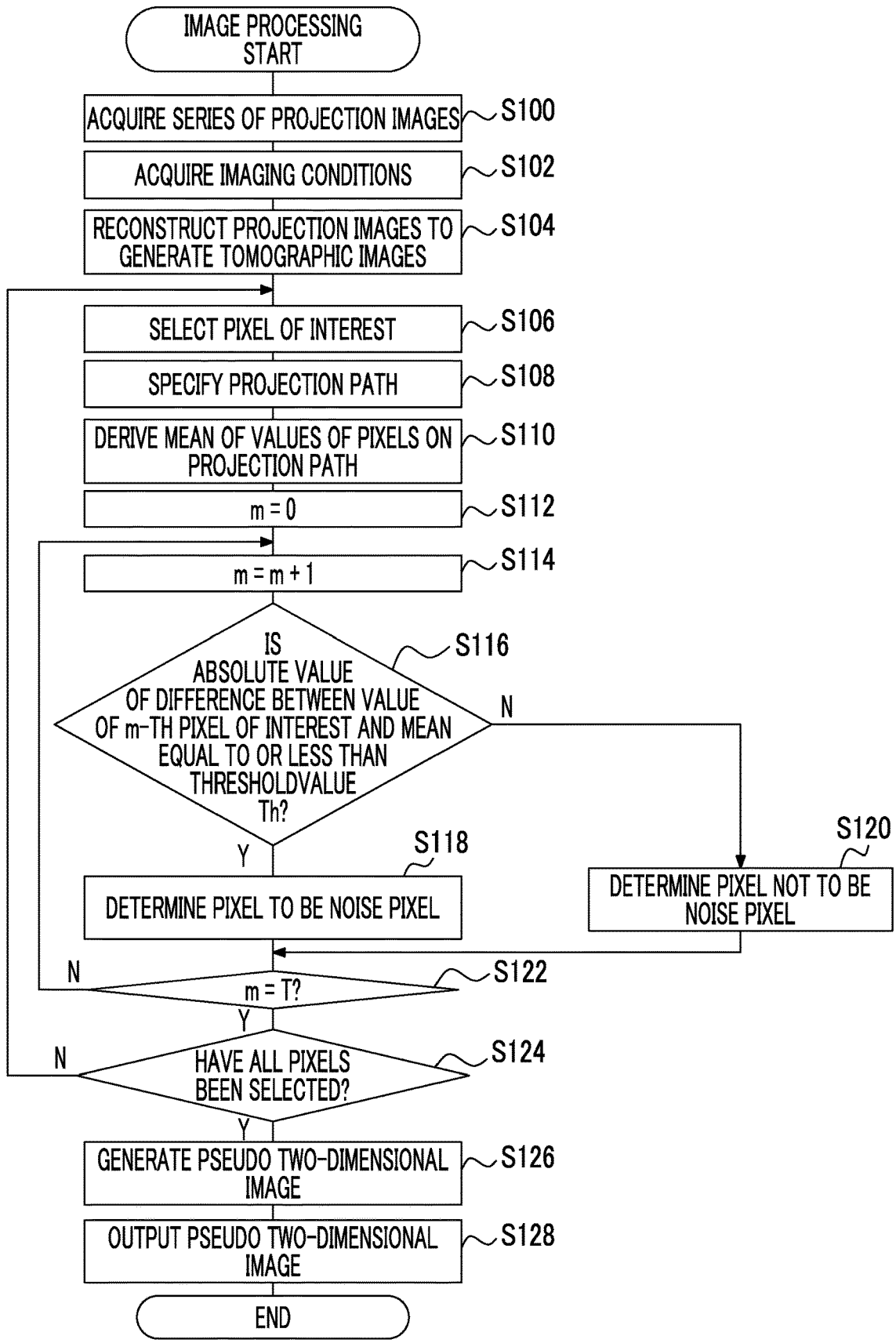
FIG. 7 is a flowchart illustrating an example of the flow of image processing performed by the console according to the first embodiment.
Figure 8:
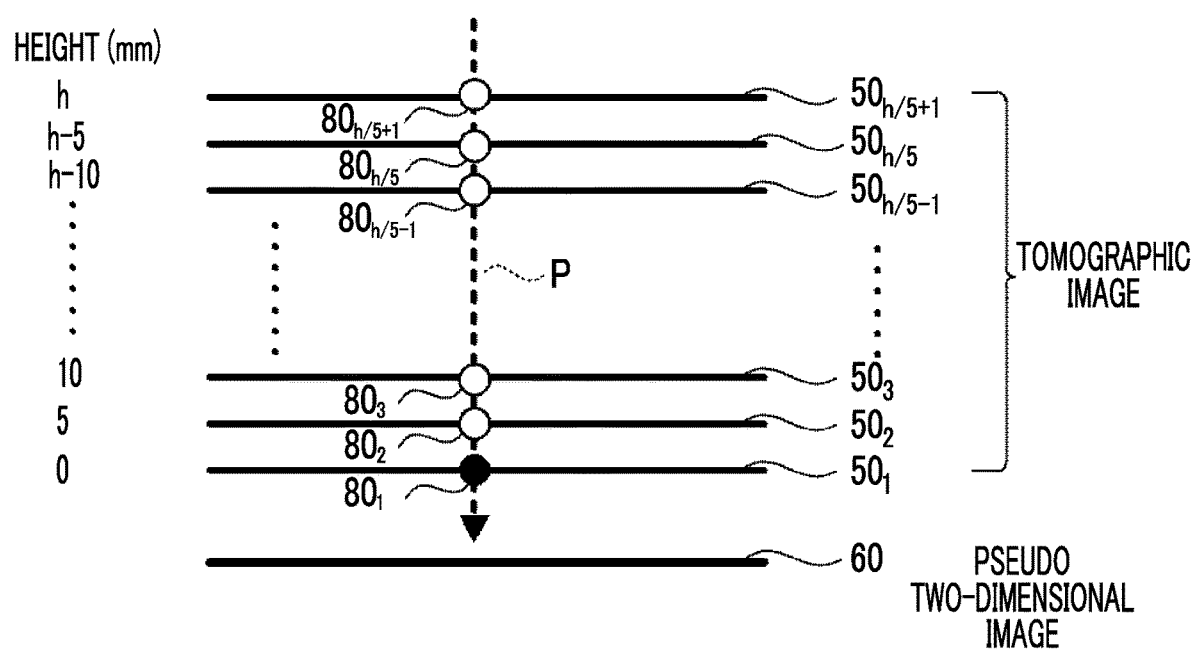
FIG. 8 is a diagram illustrating the image processing illustrated in FIG. 7.

Next, image processing for generating a pseudo two-dimensional image in the console 6 according to this embodiment will be described. FIG. 7 is a flowchart illustrating an example of the flow of the image processing performed by the control unit 40 of the console 6 according to this embodiment. FIG. 8 is a diagram illustrating the image processing illustrated in FIG. 7. FIG. 7 illustrates a case in which the tomographic images of the subject W with a height h (mm) are generated with a slice thickness of 5 (mm). In this case, the number of tomographic images is h/5+1 (a fraction is rounded up).

For example, in a case in which a command to display a pseudo two-dimensional image is received from the user through the operation unit 48 of the console 6, the CPU 40A of the control unit 40 in the console 6 according to this embodiment executes the image processing program stored in the ROM 40B to perform the image processing illustrated in FIG. 7.

As illustrated in FIG. 7, in Step S100, the control unit 40 acquires a series of projection images obtained by one tomosynthesis imaging operation. The acquisition destination of the projection image is not particularly limited as long as it is a device storing a desired projection image. For example, the acquisition destination may be the storage unit 42 of the host apparatus, the radiography apparatus 10, and a PACS.

Then, in Step S102, the control unit 40 acquires the imaging conditions of the acquired series of T projection images. The imaging conditions acquired in this step are imaging conditions corresponding to parameters required to generate a tomographic image. In this embodiment, for example, the imaging conditions are the distance between the radiation source 18 and the detection surface 22 of the radiation detector 20 and the projection angle of each projection image. The control unit 40 acquires the imaging conditions from any position or acquires the imaging conditions using any method. For example, in a case in which the imaging conditions are also stored so as to be associated with the projection images acquired in Step S100, the control unit 40 may acquire both the projection images and the imaging conditions.

Then, in Step S104, the control unit 40 reconstructs the series of projection images acquired in Step S100 to generate a series of tomographic images with a predetermined slice thickness. A method for generating a tomographic image in the control unit 40 is not particularly limited. For example, reconstruction may be performed by a back projection method, such as a filter back projection (FBP) method or an iterative reconstruction method, or a known technique may be applied. In addition, the slice thickness of the tomographic image to be generated is not particularly limited. For example, the slice thickness of the tomographic image may be predetermined according to the size of the object of interest, the quality of a radiographic image, an arithmetic processing load required for generation, and commands from the user.

Then, in Step S106, the control unit 40 selects a pixel of interest. Specifically, the control unit 40 selects the position (coordinates) of the pixel of interest in a specific second tomographic image.

In addition, a method for generating a first pseudo two-dimensional image using a series of first tomographic images in the control unit 40 is not particularly limited. For example, the first pseudo two-dimensional image may be generated by an addition method that performs an addition process of adding the values of the corresponding pixels in each tomographic image along any view direction (in this embodiment, a direction in which the irradiation angle α is 0 degrees) in a state in which the series of first tomographic images are stacked or a known technique can be applied.

Then, in Step S108, the control unit 40 specifies a projection path through which a radiation image is projected by the radiation R transmitted through the pixel of interest selected in Step S106. For example, in the example illustrated in FIG. 8, in a case in which a pixel $80_1$ of a tomographic image $50_1$ is selected as the pixel of interest, the control unit 40 specifies a projection path P passing through pixels $80_1$ to $80_{h/5+1}$. In the example illustrated in FIG. 8, the coordinates (z) of the positions of the pixels $80_1$ to $80_{h/5+1}$ in the height direction are different from each other, but the in-plane positions (x, y) of the pixels $80_1$ to $80_{h/5+1}$ are the same.

Then, in Step S110, the control unit 40 derives the mean of the values of the pixels on the projection path specified in Step S108. In the example illustrated in FIG. 8, the control unit 40 derives the mean of the values of the pixels $80_1$ to $80_{h/5+1}$.

Then, in Step S112, the control unit 40 sets a variable m for managing the number of tomographic images subjected to the noise determination to "0" (m=0). Then, in Step S114, the control unit 40 adds "1" to the variable m. Then, in Step S116, the control unit 40 determines whether the absolute value of a value obtained by subtracting the mean derived in Step S110 from the value of a pixel corresponding to an m-th pixel of interest is equal to or less than a predetermined threshold value Th.

Figure 5:
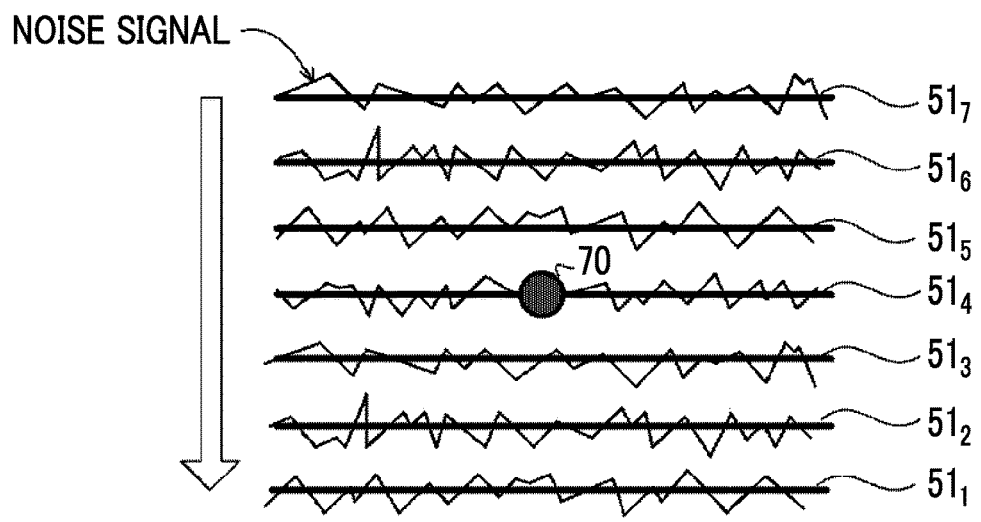
FIG. 5 is a diagram illustrating an example of the influence of signal degradation in the pseudo two-dimensional image.
Figure 6:
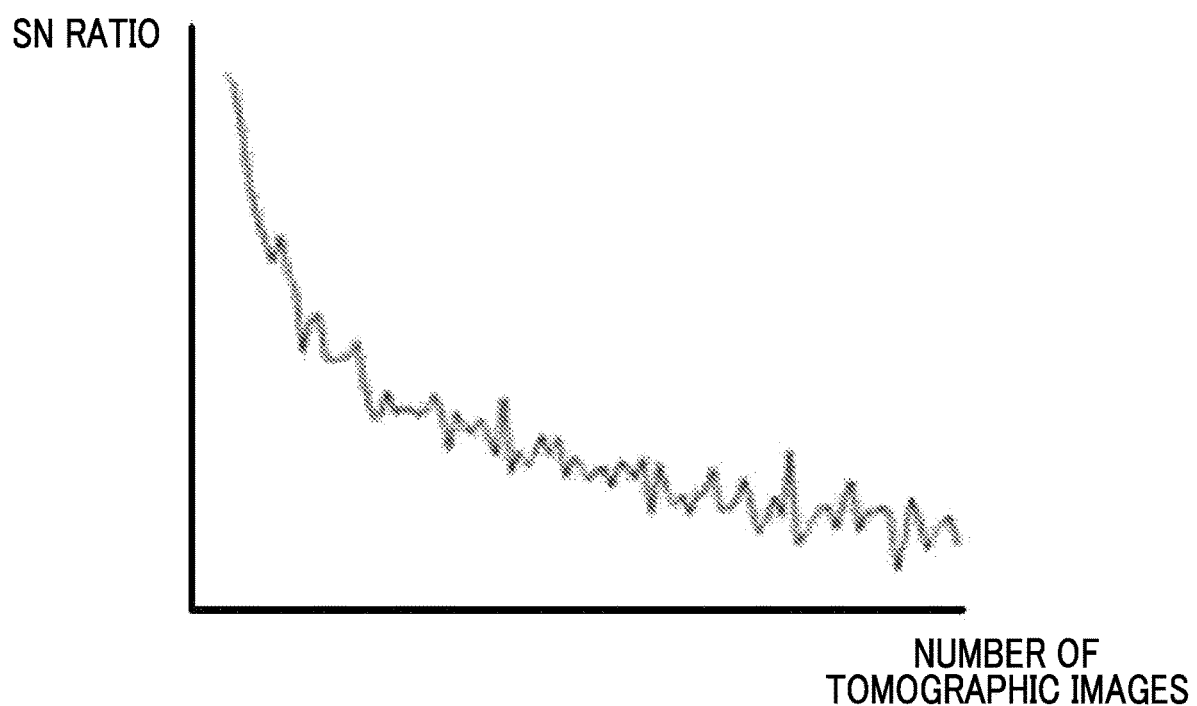
FIG. 6 is a diagram illustrating an example of the influence of the signal degradation in the pseudo two-dimensional image.

As illustrated in FIG. 5, in the pixel 70 of the object of interest, the intensity of a signal increases according to the object of interest. However, in the pixels that do not include the object of interest, a signal is affected by noise that is normally generated and the intensity of the signal tends to be relatively low. In other words, the value of the pixel 70 of the object of interest tends to be larger than the value of the pixel that does not include the object of interest and is greatly affected by noise. Therefore, in this embodiment, the mean of the values of all of the pixels on the projection path including the pixel of interest is derived and the pixel having a value, the absolute value of the difference of which from the mean of the pixel values is equal to or less than the predetermined threshold value Th, is regarded as a pixel (hereinafter, referred to as a "noise pixel") which is greatly affected by noise, such as a pixel with a high ratio of noise component. In addition, for example, the threshold value Th may be determined in advance by experiments or simulations according to the type of the object of interest which is a target object or the size of noise superimposed.

In a case in which the absolute value is equal to or less than the predetermined threshold value Th, the determination result in Step S116 is "Yes" and the control unit 40 proceeds to Step S118. In Step S118, the control unit 40 determines the pixel corresponding to the m-th pixel of interest to be the noise pixel and proceeds to Step S122. On the other hand, in a case in which the absolute value is greater than the predetermined threshold value Th, the determination result in Step S116 is "No" and the control unit proceeds to Step S120. In Step S120, the control unit 40 determines the pixel corresponding to the m-th pixel of interest not to be the noise pixel and proceeds to Step S122. In addition, the process in Step S120 may be omitted.

In Step S122, the control unit 40 determines whether the variable m is equal to the number T of tomographic images (m=T). In a case in which the variable m is not equal to the number T, that is, in a case in which there is a tomographic image that has not been subjected to the determination of whether the pixel corresponding to the pixel of interest is the noise pixel, the determination result in Step S122 is "No" and the control unit 40 returns to Step S114 and repeats the process in Steps S116 to S120. On the other hand, in a case in which the variable m is equal to the number T, the determination result in Step S122 is "Yes" and the control unit 40 proceeds to Step S124.

In Step S124, the control unit 40 determines whether all of the pixels of the specific tomographic image have been selected as the pixels of interest. In a case in which all of the pixels have not been selected as the pixels of interest, that is, in a case in which there is a pixel that has not been subjected to the noise pixel determination process, the determination result in Step S124 is "No" and the control unit 40 returns to Step S106 and repeats the process in Steps S106 to S122. On the other hand, in a case in which all of the pixels have been selected as the pixels of interest, the determination result in Step S124 is "Yes" and the control unit 40 proceeds to Step S126.

In Step S126, the control unit 40 generates a pseudo two-dimensional image using a series of tomographic images. In a case in which the control unit 40 generates the pseudo two-dimensional image using the tomographic images, the control unit 40 generates the pseudo two-dimensional image using the tomographic images from which the noise pixels have been excluded, on the basis of the determination result indicating the noise pixels. In addition, the control unit 40 may not exclude all of the noise pixels. For example, the control unit 40 may exclude the noise pixels whose ratio to the number T of second tomographic images is equal to or less than a predetermined value for the pixels on the projection path. In addition, the position of the pixel that can be excluded as the noise pixel may be predetermined. An example of the position of the pixel that can be excluded is a position that is separated from the pixel that is determined not to be the noise pixel by a predetermined distance or more.

A method for generating a pseudo two-dimensional image using a series of tomographic images in the control unit 40 is not particularly limited. For example, the pseudo two-dimensional image may be generated by an addition method that performs an addition process of adding the values of the corresponding pixels in each tomographic image along any view direction (in this embodiment, a direction in which the irradiation angle α is 0 degrees) in a state in which the series of tomographic images are stacked or a known technique can be applied.

In addition, the control unit 40 may perform, for example, predetermined filter processing for applying a low-pass filter to the tomographic image or the pseudo two-dimensional image.

Then, in Step S128, the control unit 40 outputs the pseudo two-dimensional image generated in Step S126 so as to be displayed on the display unit 46 and then ends the image processing.

As such, in the console 6 according to this embodiment, the control unit 40 acquires a plurality of projection images obtained by irradiating the subject W disposed between the radiation source 18 and the radiation detector 20 with the radiation R emitted from the radiation source 18 at different irradiation angles and capturing the radiation R with the radiation detector 20 at each irradiation angle. In addition, the control unit 40 generates a pseudo two-dimensional image by reducing the weight of the noise pixel that is more affected by noise than the pixel of the object of interest or excluding the noise pixel, using a plurality of tomographic images reconstructed from a plurality of projection images.

Therefore, according to the console 6 of this embodiment, it is possible to further improve the quality of a pseudo two-dimensional image generated using the tomographic images.

Second Embodiment

Next, a second embodiment will be described in detail. In this embodiment, the same configurations and operations as those described in the first embodiment are denoted by the same reference numerals and the detailed description thereof will not be repeated.

Since the configurations of a radiography system 1, a console 6, and a radiography apparatus 10 are the same as those in the first embodiment, the description thereof will not be repeated. In this embodiment, since image processing performed by the control unit 40 of the console 6 is different from the image processing (see FIG. 7) according to the first embodiment, different processes will be described.

Figure 9:
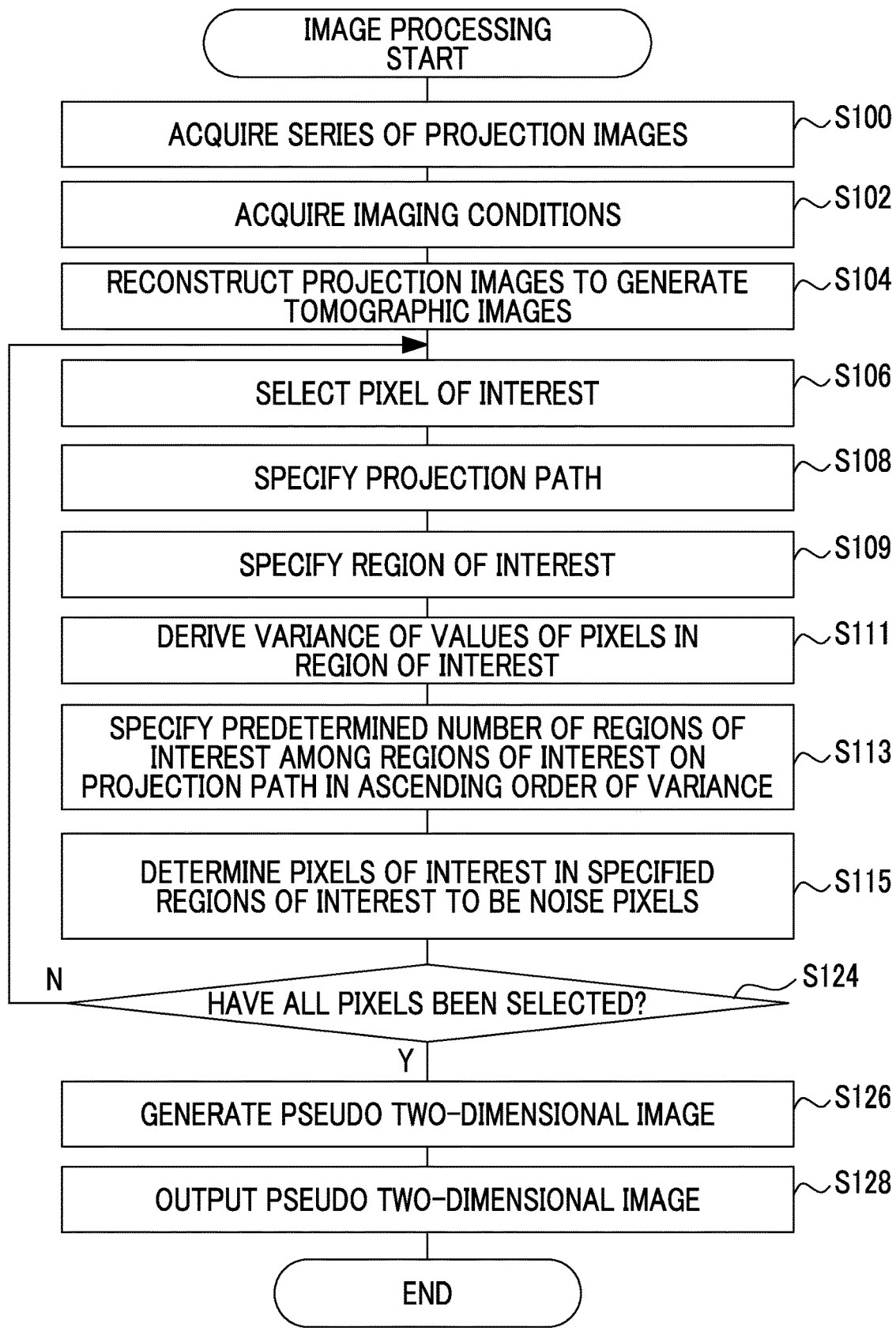
FIG. 9 is a flowchart illustrating an example of the flow of image processing performed by a console according to a second embodiment.
Figure 10:
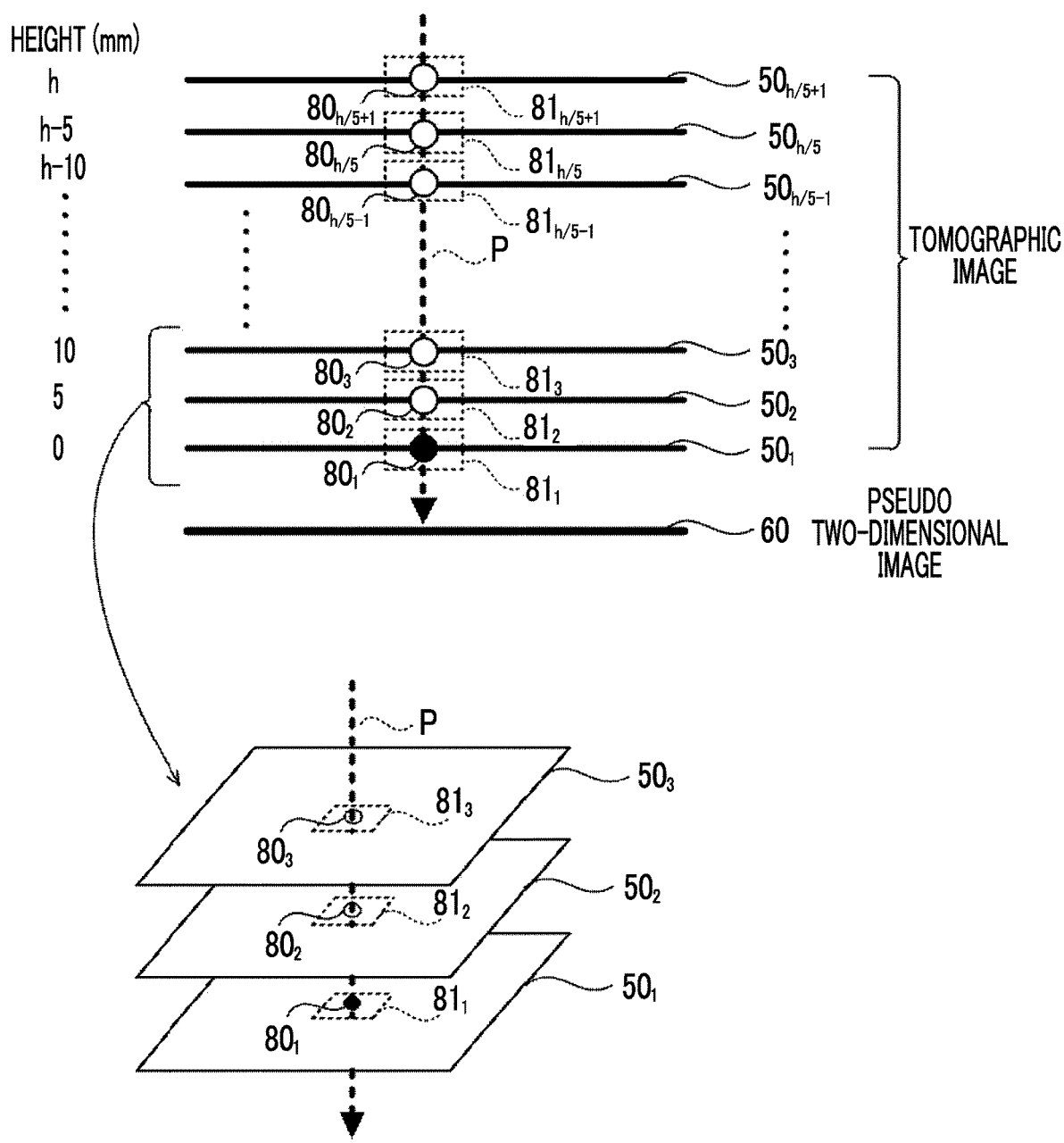
FIG. 10 is a diagram illustrating the image processing illustrated in FIG. 9.

FIG. 9 is a flowchart illustrating an example of the flow of the image processing performed by the control unit 40 according to this embodiment. FIG. 10 is a diagram illustrating the image processing illustrated in FIG. 9. FIG. 10 illustrates an example in which the tomographic images of the subject W with a height h (mm) are generated with a slice thickness of 5 (mm), similarly to the example illustrated in FIG. 8 referred to in the first embodiment.

Since the image processing illustrated in FIG. 9 includes the same processes as the image processing according to the first embodiment illustrated in FIG. 7, the same processes are denoted by the same reference numerals and the detailed description thereof will not be repeated.

The image processing illustrated in FIG. 9 differs from the image processing illustrated in FIG. 7 in that a process in Steps S109 to S115 is performed instead of the process in Steps S110 to S122.

In Step S109, the control unit 40 specifies a region of interest in each of the series of tomographic images generated in Step S104. Specifically, the control unit 40 specifies, as the region of interest, a region with a predetermined size including a pixel corresponding to the pixel of interest in the plane in each of the series of tomographic images. In the example illustrated in FIG. 10, in a case in which a pixel $80_1$ of a tomographic image $50_1$ is selected as the pixel of interest, the control unit 40 specifies regions of interest $81_1$ to $81_{h/5+1}$ including the pixels $80_1$ to $80_{h/5+1}$, respectively. In the example illustrated in FIG. 10, the coordinates (z) of the positions of the regions of interest $81_1$ to $81_{h/5+1}$ in the height direction are different from each other, but the in-plane positions (x, y) of the regions of interest $81_1$ to $81_{h/5+1}$ are the same. In addition, the size of the region of interest or the position of the pixel of interest in the region of interest is not particularly limited. For example, the size of the region of interest may be determined according to the size of the object of interest which is a measurement target. In addition, for example, the pixel of interest may be located at the center of the region of interest.

Then, in Step S111, the control unit 40 derives the variance of the values of the pixels included in each of the regions of interest specified in Step S109. In the example illustrated in FIG. 10, the control unit 40 derives a variance $\sigma^2(x, y, z)$ of the pixel values in each of the regions of interest $81_1$ to $81_{h/5+1}$ using the following Expression (1). In the following Expression (1), "ROI" indicates the region of interest:

$$\sigma^2(x, y, z) = \sum_{i \in ROI} r(x_i, y_i, z_i)^2. \quad (1)$$

Then, in Step S113, the control unit 40 specifies a predetermined number of regions of interest in ascending order of the variance among the regions of interest on the projection path. In the first embodiment, as described above, in the pixel of the object of interest, the intensity of a signal increases according to the object of interest. In the pixels that do not include the object of interest and are greatly affected by noise, that is, the noise pixels, the intensity of a signal tends to be low. Therefore, for the variance of the values of the pixels included in the region of interest, the variance tends to be large in the region of interest including the pixel of the object of interest and tends to be small in the region of interest that does not include the pixel of the object of interest. The pixel of interest included in the region of interest that does not include the pixel of the object of interest is regarded as the noise pixel. Therefore, first, the control unit 40 specifies a predetermined number of regions of interest in ascending order of the variance. In addition, the predetermined number of regions of interest is not particularly limited. For example, the number of regions of interest may correspond to a predetermined ratio with respect to the number T of second tomographic images.

Then, in Step S115, the control unit 40 determines the pixel of interest included in the region of interest specified in Step S113 to be the noise pixel.

As such, the console 6 according to this embodiment determines the pixel of interest, which is included in at least one region of interest selected from the corresponding regions of interest on a specific projection path in ascending order of the variance of the values of the pixels in the region of interest, to be the noise pixel.

Therefore, according to this embodiment, it is possible to determine the noise pixel for each region of interest and to more appropriately determine the noise pixel.

Third Embodiment

Next, a third embodiment will be described in detail. In this embodiment, the same configurations and operations as those described in the first embodiment are denoted by the same reference numerals and the detailed description thereof will not be repeated.

In the first embodiment, as described above, in general, the pseudo two-dimensional image tends to have a lower image quality than the two-dimensional image obtained by the simple imaging.

Figure 11:
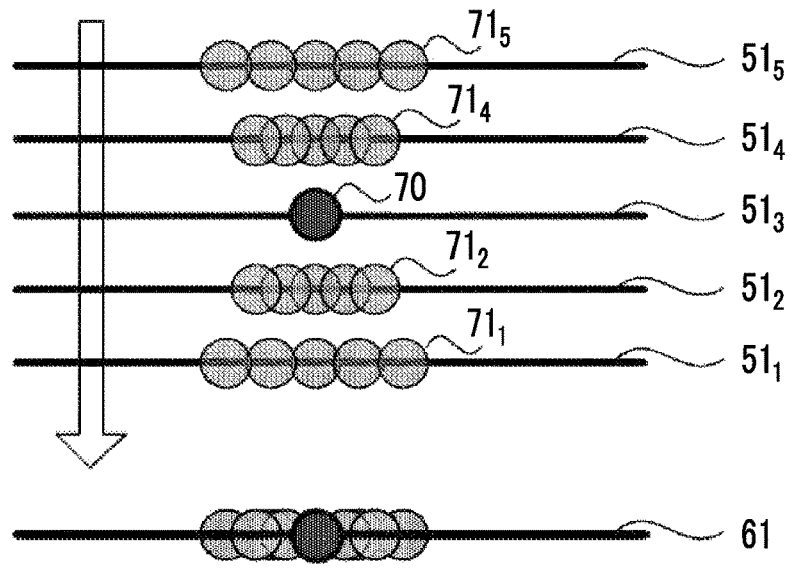
FIG. 11 is a diagram illustrating an example of the influence of a ripple artifact in a pseudo two-dimensional image.

For example, the quality of the pseudo two-dimensional image is degraded by the influence of a ripple artifact (residual image) in addition to the above-mentioned influence of noise. The ripple artifact will be described with reference to FIG. 11. In the tomosynthesis imaging, the angle at which the radiation R is emitted is limited. Therefore, for example, even in a case in which the projection images are simply superimposed by a back projection method to reconstruct a tomographic image, a virtual image (residual image) of the object is likely to be included in a region in which no objects are originally present. Even in a case in which the tomographic image is reconstructed by other methods, the same problem occurs. As such, in some cases, the ripple artifact is generated in the tomographic image obtained by the tomosynthesis imaging in a depth direction. For example, in the case illustrated in FIG. 11, for a pixel 70 of a tomographic image $51_3$, ripple artifacts $71_1$, $71_2$, $71_4$, and $71_5$ are generated in tomographic images $51_1$, $51_2$, $51_4$, and $51_5$, respectively. Therefore, in a pseudo two-dimensional image 61 generated by the tomographic image $51_1$ to $51_5$, the ripple artifacts $71_1$ to $71_5$ are added and the pseudo two-dimensional image 61 is blurred.

As described in, for example, JP5952251B, in a case in which an image is represented by a spatial frequency range, the ripple artifacts in the depth direction tend to increase as the object has a lower frequency component and the width of the subject W (a direction intersecting the height direction) increases. In addition, the influence range of the ripple artifacts becomes wider as the thickness of the subject W becomes larger. Therefore, the influence of blurring by the ripple artifacts in the pseudo two-dimensional image increases.

In addition, as the angle at which the radiation R is emitted becomes larger, a residual image is more likely to be included in a region separated from the region in which an object is originally present. In a case in which the tomographic images reconstructed from the projection images are added, a ripple artifact that looks like an object extending in the depth direction is generated in the range in which the regions irradiated with the radiation R overlap each other in the depth direction.

For this reason, in a case in which a pseudo two-dimensional image is generated, the console 6 according to this embodiment performs image processing for preventing the ripple artifacts for the projection image with a low-frequency component that is greatly affected by the ripple artifacts in order to prevent the influence of the ripple artifacts.

Figure 12:
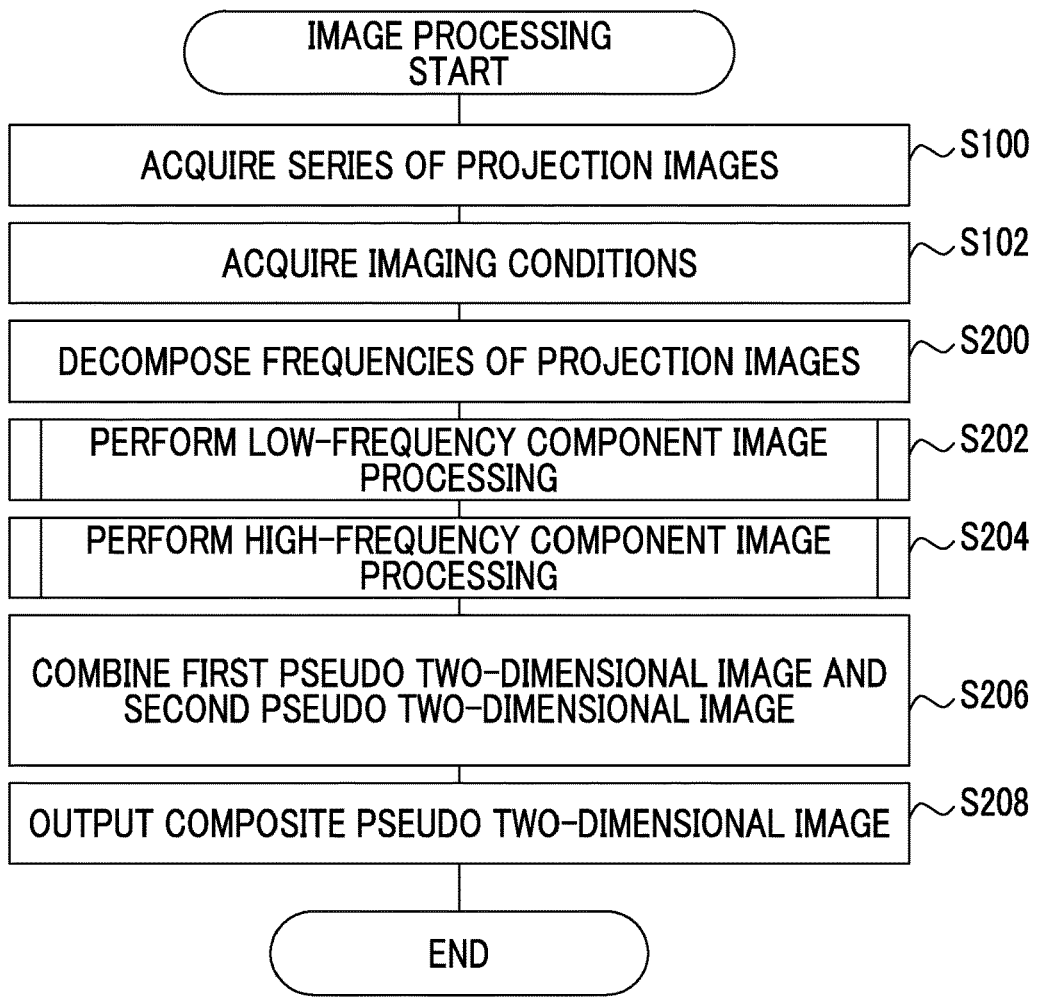
FIG. 12 is a flowchart illustrating an example of the flow of image processing performed by a console according to a third embodiment.
Figure 13:
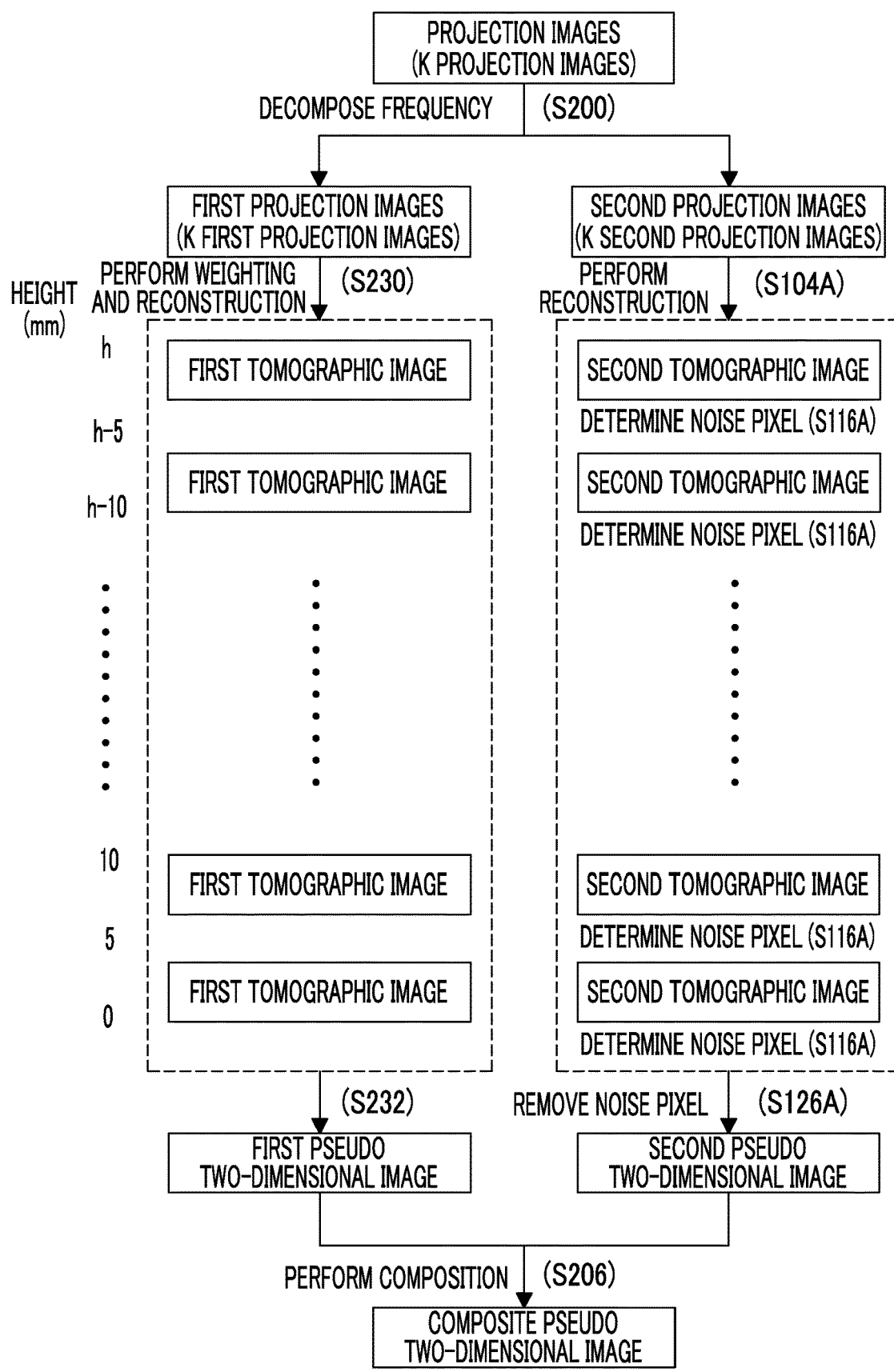
FIG. 13 is a diagram schematically illustrating a radiographic image generated by the console with the execution of the image processing illustrated in FIG. 12.

FIG. 12 is a flowchart illustrating an example of the flow of the image processing performed by the control unit 40 according to this embodiment. FIG. 13 schematically illustrates a radiographic image generated by the console 6 with the execution of the image processing illustrated in FIG. 12.

Since the image processing illustrated in FIG. 12 includes the same processes as the image processing according to the first embodiment illustrated in FIG. 7, the same processes are denoted by the same reference numerals and the detailed description thereof will not be repeated.

The image processing illustrated in FIG. 12 differs from the image processing illustrated in FIG. 7 in that a process in Steps S200 to S208 is performed instead of the process in Steps S104 to S128.

In Step S200, the control unit 40 decomposes the frequency of each of the series of projection images acquired in Step S100 to derive a first projection image with a low-frequency component and a second projection image with a high-frequency component which have different spatial frequency bands. The control unit 40 according to this embodiment functions as an example of a decomposition unit according to the present disclosure. In this embodiment, in a case in which the "first projection image" and the "second projection image" are generically referred to without being distinguished from each other, they are simply referred to as "projection images".

The "low frequency" means a frequency component including a structure with a size of about 1 (cm) in consideration of a relatively small object of interest such as calcification or a microstructure of bone. However, the "low frequency" is not particularly limited. In contrast, the "high frequency" means a frequency component higher than the low frequency. In addition, a low frequency band and a high frequency band may partially overlap each other.

A method for decomposing the frequency of the projection image in the control unit 40 is not particularly limited. For example, methods, such as Laplacian pyramid decomposition, Fourier transform, wavelet transform, and unsharp mask, can be applied.

Figure 14:
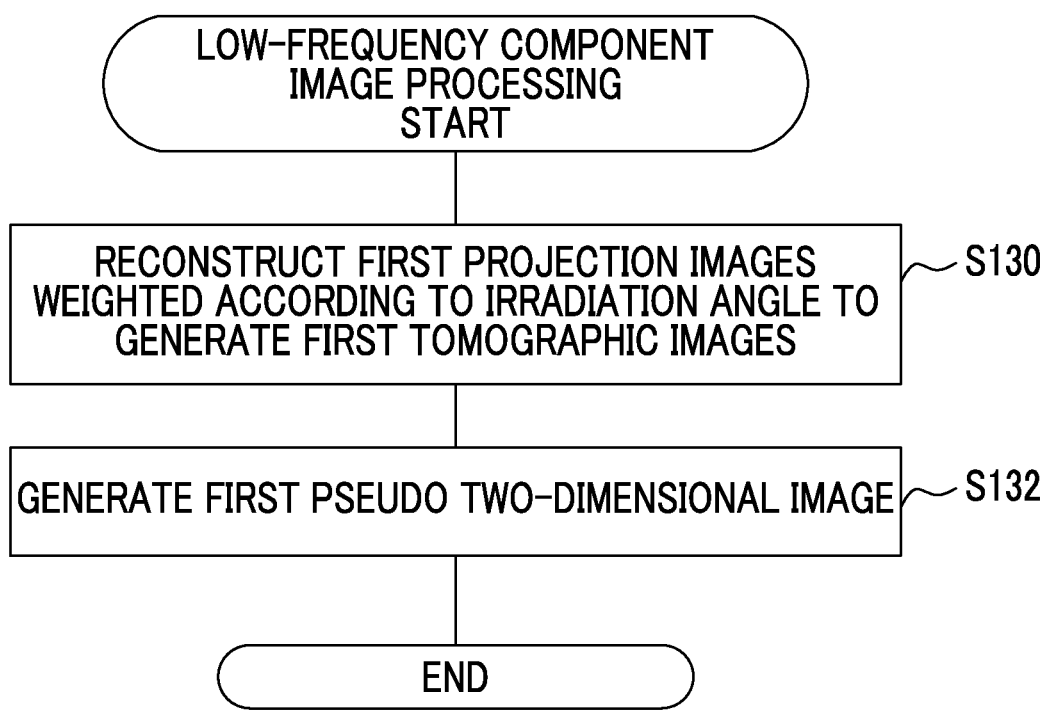
FIG. 14 is a flowchart illustrating an example of the flow of low-frequency component image processing in the image processing performed by the console according to the third embodiment.

Then, in Step S202, the control unit 40 performs low-frequency component image processing for preventing the influence of the ripple artifacts from a series of first projection images which are the projection images with a low-frequency component. FIG. 14 is a flowchart illustrating an example of the flow of the low-frequency component image processing performed by the control unit 40 according to this embodiment.

In Step S230 illustrated in FIG. 14, the control unit 40 reconstructs a series of first projection images weighted according to the angle at which the radiation R is emitted to generate a series of first tomographic images with a predetermined slice thickness. In this embodiment, there are a plurality of types of tomographic images including the "first tomographic image" and a "second tomographic image" which will be described in detail below. However, in a case in which the plurality of types of tomographic images are generically referred to without being distinguished from each other, they are simply referred to as "tomographic images".

As described above, as the angle at which the radiation R is emitted becomes larger, the influence of the ripple artifacts becomes larger. Therefore, the control unit 40 gives a smaller weight as the first projection image is captured at a larger irradiation angle to reconstruct the series of first projection images. In addition, a method for generating the first tomographic image from a series of projection images in the control unit 40 and the slice thickness are not particularly limited. For example, the method and the slice thickness may be the same as those in Step S104 (see FIG. 7) in the image processing according to the first embodiment.

Then, in Step S232, the control unit 40 generates a first pseudo two-dimensional image using the series of first tomographic images generated in Step S230 and then ends the low-frequency component image processing. In addition, a method for generating the first pseudo two-dimensional image using a series of first tomographic images in the control unit 40 is not particularly limited. For example, the first pseudo two-dimensional image may be generated by the same method as that in Step S126 (see FIG. 7) in the image processing according to the first embodiment.

In the image processing according to this embodiment, in a case in which the low-frequency component image processing in Step S202 ends in this way, the control unit 40 proceeds to Step S204.

Figure 15:
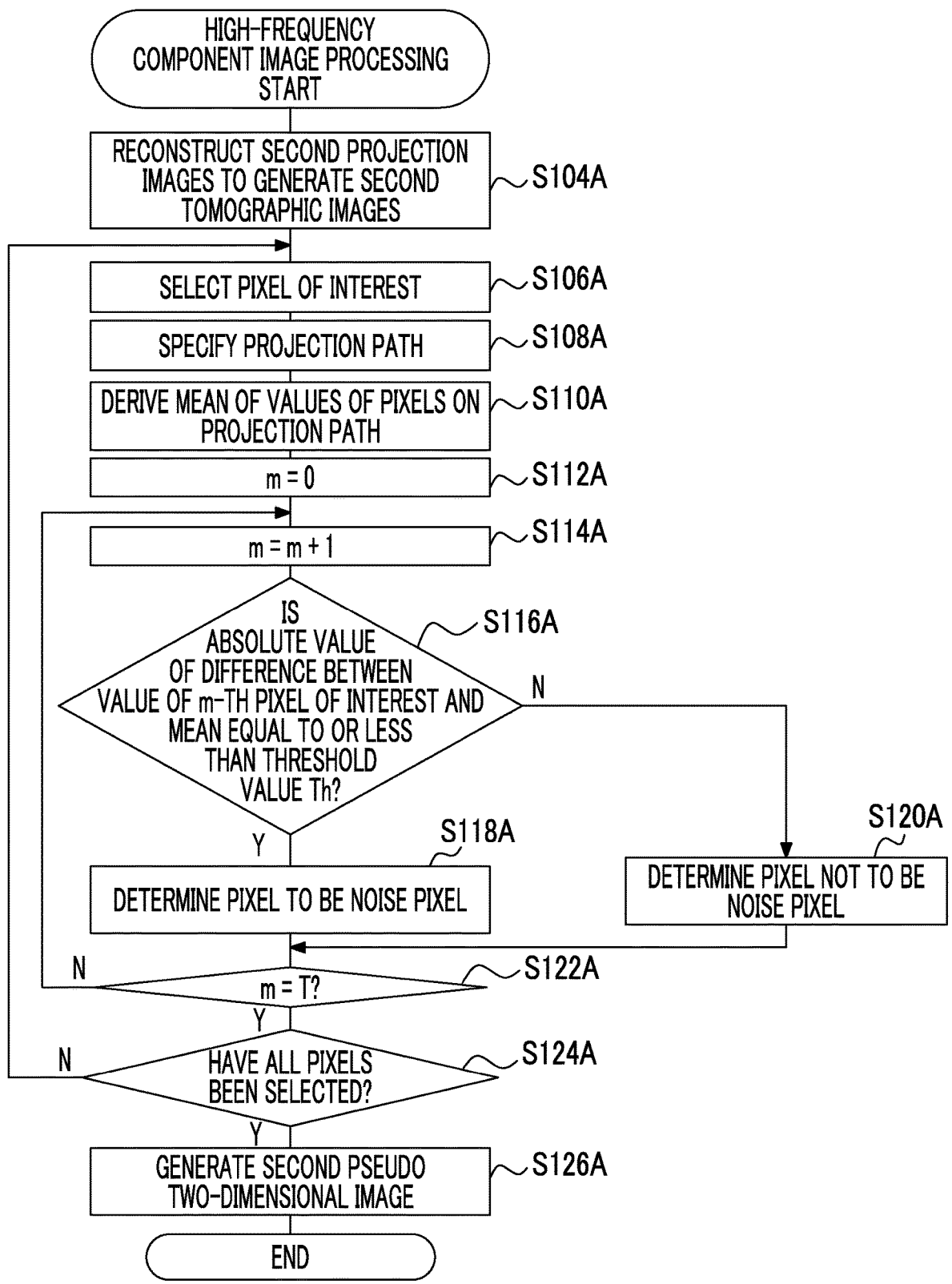
FIG. 15 is a flowchart illustrating an example of the flow of high-frequency component image processing in the image processing performed by the console according to the third embodiment.

In Step S204, the control unit 40 performs high-frequency component image processing for preventing the influence of the signal degradation from a series of second projection images which are the projection images with a high-frequency component. FIG. 15 is a flowchart illustrating an example of the flow of the high-frequency component image processing performed by the control unit 40 according to this embodiment.

As illustrated in FIG. 15, in the high-frequency component image processing according to this embodiment, processes in Steps S104A to S126A are performed. The processes in Steps S104A to S126A correspond to the processes in Steps S104 to S126 in the image processing according to the first embodiment. Since the processes are the same as those in the first embodiment except that the "projection image" is replaced with a "second projection image", the "tomographic image" is replaced with a "second tomographic image", and the "pseudo two-dimensional image" is replaced with a "second pseudo two-dimensional image", the detailed description thereof will not be repeated. Hereinafter, for example, in a case in which the first pseudo two-dimensional image and the second pseudo two-dimensional image are generically referred to without being distinguished from each other, they are simply referred to as "pseudo two-dimensional images".

In the image processing according to this embodiment, in a case in which the high-frequency component image processing in Step S204 ends in this way, the control unit 40 proceeds to Step S206. In addition, the order of the low-frequency component image processing in Step S202 and the high-frequency component image processing in Step S204 is not limited to this embodiment.

In Step S206, the control unit 40 combines the first pseudo two-dimensional image generated in Step S202 and the second pseudo two-dimensional image generated in Step S204 to generate a pseudo two-dimensional image (hereinafter, referred to as a "composite pseudo two-dimensional image"). In addition, the control unit 40 may perform, for example, predetermined filter processing for applying a low-pass filter to the second pseudo two-dimensional image and then combine the second pseudo two-dimensional image and the first pseudo two-dimensional image.

Then, in Step S208, the control unit 40 outputs the composite pseudo two-dimensional image generated in Step S206 so as to be displayed on the display unit 46 and then ends the image processing.

Fourth Embodiment

Next, a fourth embodiment will be described in detail. In this embodiment, the same configurations and operations as those described in the first embodiment are denoted by the same reference numerals and the detailed description thereof will not be repeated.

Since the configurations of a radiography system 1, a console 6, and a radiography apparatus 10 are the same as those in the first embodiment, the description thereof will not be repeated. In this embodiment, image processing performed by the control unit 40 of the console 6 differs from the image processing (see FIG. 12) according to the third embodiment in some processes. Therefore, different processes will be described.

Figure 16:
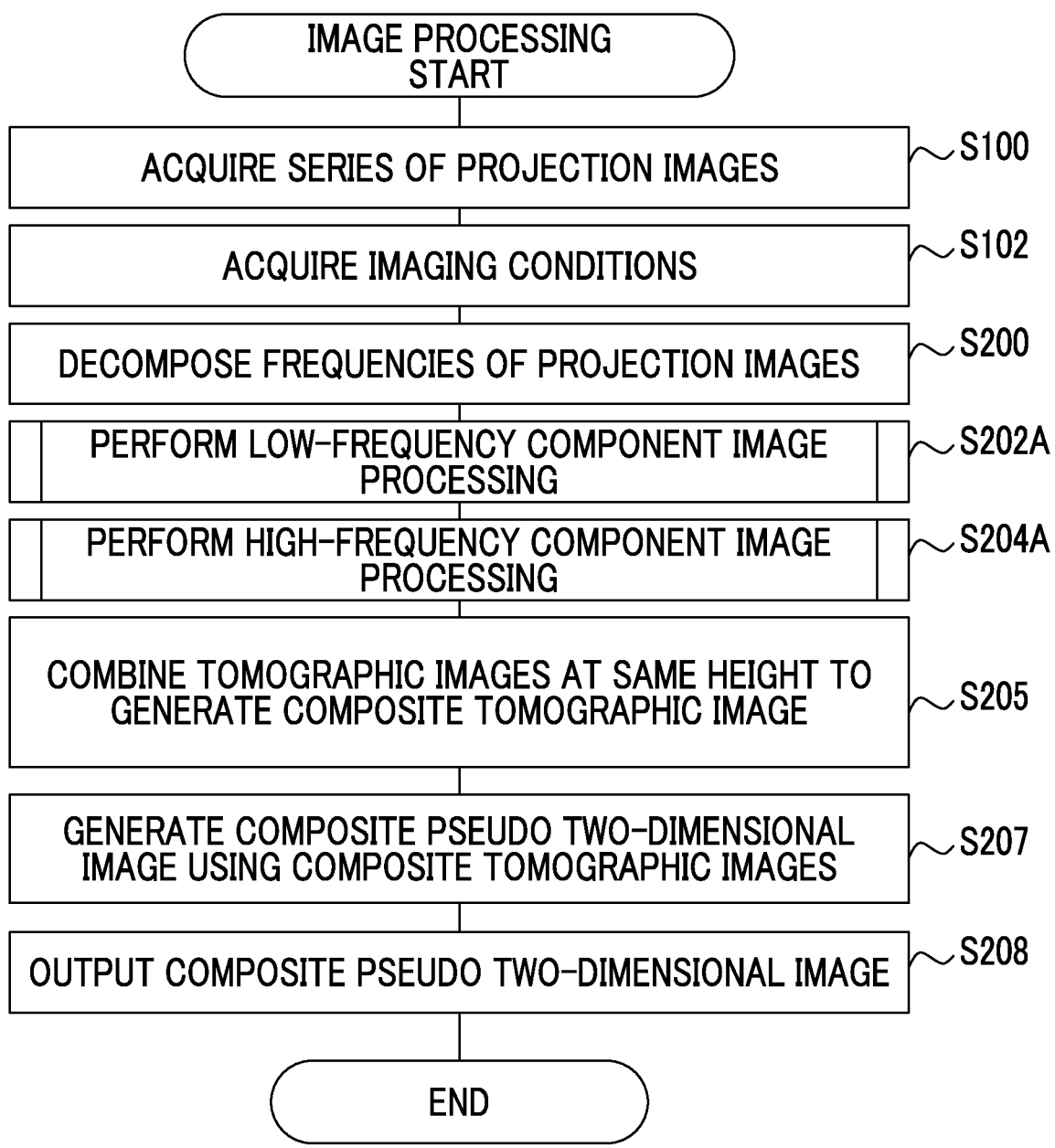
FIG. 16 is a flowchart illustrating an example of the flow of image processing performed by a console according to a fourth embodiment.
Figure 17:
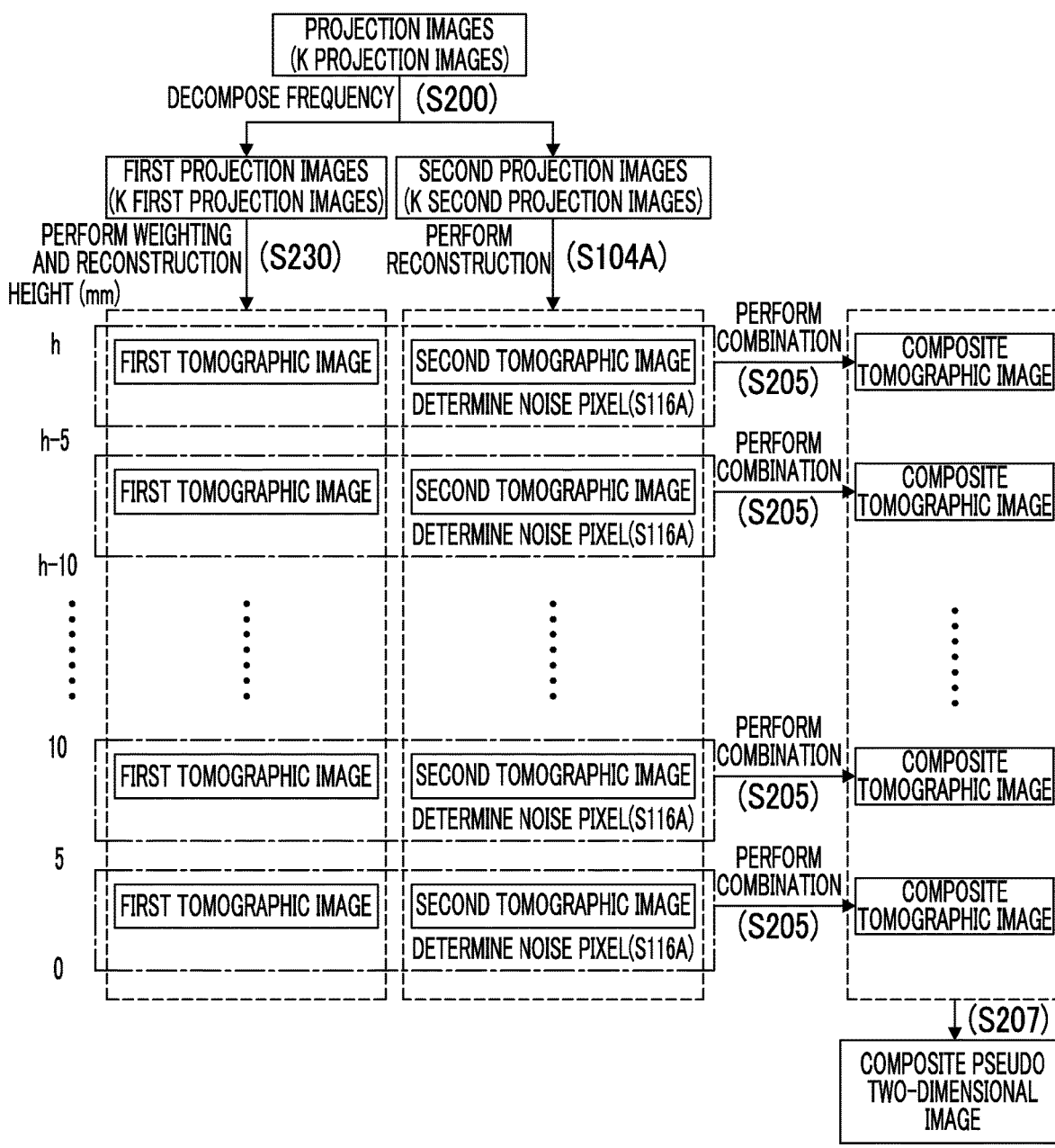
FIG. 17 is a diagram schematically illustrating a radiographic image generated by the console with the execution of the image processing illustrated in FIG. 16.

FIG. 16 is a flowchart illustrating an example of the flow of the image processing performed by the control unit 40 of the console 6 according to this embodiment. FIG. 17 schematically illustrates a radiographic image generated by the console 6 with the execution of the image processing operation illustrated in FIG. 16.

In the third embodiment, the control unit 40 of the console 6 generates the first pseudo two-dimensional image using a series of first tomographic images, generates the second pseudo two-dimensional image using a series of second tomographic images, and combines the first pseudo two-dimensional image and the second pseudo two-dimensional image to generate the composite pseudo two-dimensional image. In contrast, the control unit 40 of the console 6 according to this embodiment combines each of a series of first tomographic images and each of a series of second tomographic images according to height to generate a series of composite tomographic images and generates a pseudo two-dimensional image using the composite tomographic images, as illustrated in FIGS. 16 and 17.

The image processing according to this embodiment illustrated in FIG. 16 differs from the image processing (see FIG. 12) according to the third embodiment in that processes in Steps S202A and S204A are performed instead of the processes in Steps S202 and S204.

Figure 18:
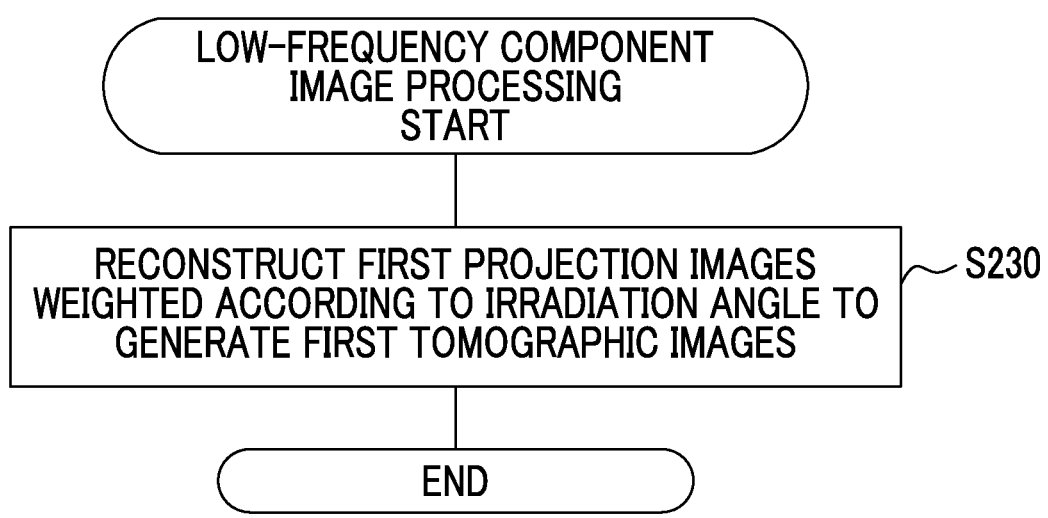
FIG. 18 is a flowchart illustrating an example of the flow of low-frequency component image processing in the image processing performed by the console according to the fourth embodiment.

The process in Step S202A is the same as the process in Step S202 in the image processing according to the third embodiment in that low-frequency component image processing for preventing the influence of the ripple artifacts from a series of first projection images which are projection images with a low-frequency component is performed and differs from the process in Step S202 in a portion of the flow of a specific process. FIG. 18 is a flowchart illustrating an example of the flow of the low-frequency component image processing performed by the control unit 40 according to this embodiment.

As illustrated in FIG. 18, the low-frequency component image processing according to this embodiment differs from the low-frequency component image processing (see FIG. 14) according to the third embodiment in that only a process in Step S230 is performed (the process in Step S232 is not performed). That is, in the low-frequency component image processing according to this embodiment, the pseudo two-dimensional image (first pseudo two-dimensional image) is not generated.

Figure 19:
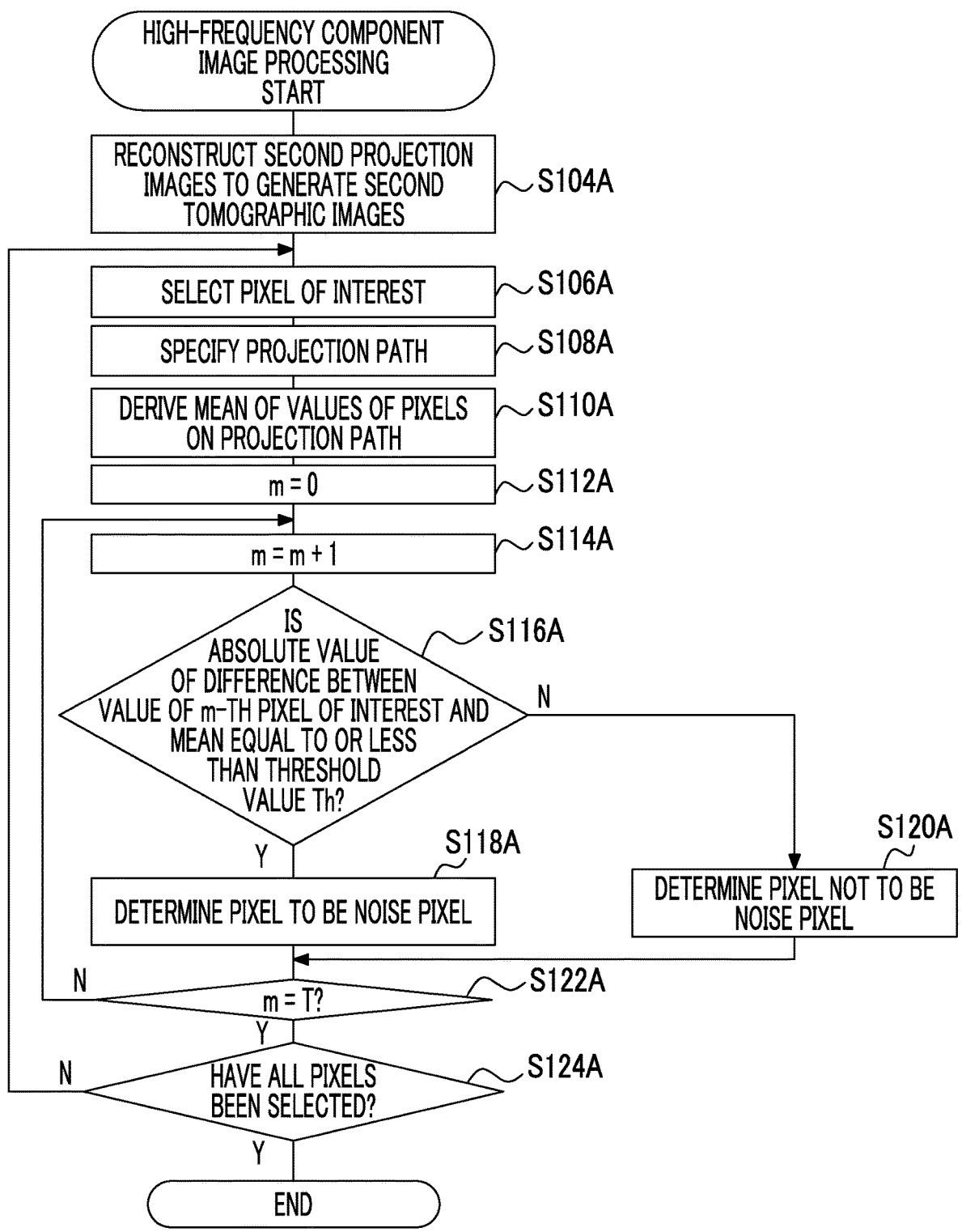
FIG. 19 is a flowchart illustrating an example of the flow of high-frequency component image processing in the image processing performed by the console according to the fourth embodiment.

In addition, a process in Step S204A is the same as the process in Step S204 in the image processing according to the third embodiment in that high-frequency component image processing for preventing the influence of the signal degradation from a series of second projection images which are projection images with a high-frequency component is performed and differs from the process in Step S204 in a portion of the flow of a specific process. FIG. 19 is a flowchart illustrating an example of the flow of the high-frequency component image processing performed by the control unit 40 according to this embodiment.

As illustrated in FIG. 19, the high-frequency component image processing according to this embodiment differs from the high-frequency component image processing (see FIG. 15) according to the third embodiment in that only the processes in Steps S104A to S124A are performed (the process in Step S126A is not performed). That is, in the high-frequency component image processing according to this embodiment, the pseudo two-dimensional image (second pseudo two-dimensional image) is not generated.

The image processing according to this embodiment illustrated in FIG. 16 differs from the image processing (see FIG. 12) according to the third embodiment in that the processes in Steps S205 and S207 are performed instead of the process in Step S206.

In Step S205, the control unit 40 combines the pixels at the corresponding position in the first tomographic image and the second tomographic image at the same height among a series of first tomographic images and a series of second tomographic images to generate a series of composite pseudo two-dimensional images. In the generation of the composite pseudo two-dimensional image, the control unit 40 uses the second tomographic images from which the noise pixels have been excluded, as in the generation of the second pseudo two-dimensional image in Step S126A according to the third embodiment. Therefore, according to this step, a series of composite tomographic images from which the noise pixel has been removed is generated. In addition, for example, predetermined filter processing for applying a low-pass filter may be performed for the second tomographic image from which the noise pixel has been removed and the second tomographic image may be combined with the first tomographic image.

Then, in Step S207, the control unit 40 generates a composite pseudo two-dimensional image using the series of composite tomographic images generated in Step S207. A method for generating a composite pseudo two-dimensional image using a series of composite tomographic images in the control unit 40 is not particularly limited. For example, the composite pseudo two-dimensional image may be generated by an addition method that performs an addition process of adding the values of the corresponding pixels in each composite tomographic image along any view direction (in this embodiment, a direction in which the irradiation angle α is 0 degrees) in a state in which the series of composite tomographic images are stacked or a known technique can be applied.

As described above, in the console 6 according to each of the above-mentioned embodiments, the control unit 40 functions as an acquisition unit and a generation unit according to the present disclosure. The control unit 40 acquires a plurality of projection images obtained by irradiating the subject W disposed between the radiation source 18 and the radiation detector 20 with the radiation R emitted from the radiation source 18 at different irradiation angles and capturing the radiation R with the radiation detector 20 at each irradiation angle. In addition, the control unit 40 generates a pseudo two-dimensional image by reducing the weight of the noise pixel that is more affected by noise than the pixel of the object of interest or excluding the noise pixel, using a plurality of tomographic images reconstructed from a plurality of projection images.

Therefore, according to the console 6 of each of the above-described embodiments, it is possible to further improve the quality of a pseudo two-dimensional image generated using the tomographic images.

In each of the above-described embodiments, the addition method is applied as the method for generating the pseudo two-dimensional image in the control unit 40. However, as described above, other known techniques can be applied. For example, a so-called minimum path method using the minimum value of the corresponding pixels in each tomographic image may be applied. In this case, since the minimum value of the pixel values after the noise pixel is excluded is used, it is possible to select a more appropriate pixel.

In each of the above-described embodiments, the second tomographic image from which the noise pixel has been excluded is used. However, the handling of the noise pixel is not limited thereto. For example, the noise pixel may not be excluded and the weight of the noise pixel may be less than those of other pixels (the pixels determined not to be the noise pixel).

In each of the above-described embodiments, in the simple imaging, the radiation source 18 emits the radiation R at the irradiation position where the irradiation angle α is 0 degrees to perform imaging. However, the invention is not limited to each of the above-described embodiments as long as the radiation source 18 emits the radiation R at a fixed position without being moved.

In each of the above-described embodiments, various processors other than the CPU may perform the image processing performed by the execution of software (program) by the CPU. In this case, examples of the processor include a programmable logic device (PLD) whose circuit configuration can be changed after manufacture, such as a field-programmable gate array (FPGA), and a dedicated electric circuit, such as an application specific integrated circuit (ASIC), which is a processor having a dedicated circuit configuration designed to perform a specific process. In addition, the image processing may be performed by one of the various processors or may be performed by a combination of two or more processors of the same type or different types (for example, a combination of a plurality of FPGAs and a combination of a CPU and an FPGA). Specifically, the hardware structure of the various processors is an electric circuit obtained by combining circuit elements such as semiconductor elements.

In each of the above-described embodiments, the aspect in which various programs stored in the control unit 30 of the radiography apparatus 10 and the control unit 40 of the console 6 are stored (installed) in the ROMs (30B and 40B) of the control unit 30 and the control unit 40 in advance has been described. However, the invention is not limited thereto. The image processing program may be recorded on a recording medium, such as a compact disk read only memory (CD-ROM), a digital versatile disk read only memory (DVD-ROM), or a universal serial bus (USB) memory, and then provided. In addition, the image processing program may be downloaded from an external apparatus through the network.

In each of the above-described embodiments, the radiation R is not particularly limited. For example, X-rays or γ-rays may be applied.

In addition, for example, the configurations and operations of the radiography system 1, the console 6, and the radiography apparatus 10 according to each of the above-described embodiments are illustrative and may be changed according to the situation, without departing from the scope and spirit of the invention. In addition, the above-described embodiments may be appropriately combined with each other.

EXPLANATION OF REFERENCES

1: radiography system
6: console

9t: irradiation position
10: radiography apparatus
12: imaging table
14: imaging surface
16: radiation emitting unit
18: radiation source
19: radiation source driving unit
20: radiation detector
22: detection surface
30, 40: control unit
30A, 40A: CPU
30B, 40B: ROM
30C, 40C: RAM
32, 42: storage unit
34, 44: I/F unit
36: operation panel
39, 49: bus
46: display unit
48: operation unit
$50_1$ to $50_{h/5+1}$, $51_1$ to $51_5$: tomographic image
60, 61: pseudo two-dimensional image
70, $80_1$ to $80_{h/5+1}$: pixel
$71_1$ to $71_5$: ripple artifact
$81_1$ to $81_{h/5+1}$: region of interest
CL: normal line
P: projection path
r: projection direction
R: radiation
RC: radiation axis
W: subject
α, θ: angle

What is claimed is:

1. An image processing apparatus comprising:
a processor configured to
acquire a plurality of projection images obtained by irradiating a subject disposed between a radiation source and a radiation detector with radiation emitted from the radiation source at different irradiation angles and capture the radiation with the radiation detector at each of the irradiation angles;
generate a plurality of tomographic images reconstructed from the plurality of projection images;
in the plurality of tomographic images, perform a noise processing of reducing a weight of a noise pixel which is more affected by noise with respect to corresponding pixels on a specific projection path or excluding the noise pixel, wherein the specific projection path is a projection path through which a radiation image is projected by the radiation passing through a pixel of an object of interest; and
generate a pseudo two-dimensional image using the plurality of tomographic images after the noise processing.

2. The image processing apparatus according to claim 1, wherein the processor determines a pixel having a value, whose difference from a mean of values of corresponding pixels on a specific projection path in the plurality of tomographic images is equal to or less than a predetermined threshold value, to be the noise pixel.

3. The image processing apparatus according to claim 2, wherein, in a case in which a plurality of noise pixels are present on the projection path, the processor reduces the weights of some of the noise pixels or excludes some of the noise pixels.

4. The image processing apparatus according to claim 3, wherein a ratio of a number of the some noise pixels of the plurality of noise pixels to a number of tomographic images is equal to or less than a predetermined value.

5. The image processing apparatus according to claim 1, wherein the processor determines a pixel of interest, which is included in a region of interest having a smaller variance of pixel values than other regions of interest among corresponding regions of interest including the pixels of interest on a projection path in the plurality of tomographic images, to be the noise pixel.

6. The image processing apparatus according to claim 5, wherein, in a case in which a plurality of noise pixels are present on the projection path, the processor reduces the weights of some of the noise pixels or excludes some of the noise pixels.

7. The image processing apparatus according to claim 6, wherein a ratio of a number of the some noise pixels of the plurality of noise pixels to a number of tomographic images is equal to or less than a predetermined value.

8. The image processing apparatus according to claim 1, wherein, in a case in which a plurality of noise pixels are present on the projection path, the processor reduces the weights of some of the noise pixels or excludes some of the noise pixels.

9. The image processing apparatus according to claim 8, wherein a ratio of a number of the some noise pixels of the plurality of noise pixels to a number of tomographic images is equal to or less than a predetermined value.

10. An image processing method using the image processing apparatus according to claim 1 comprising:
acquiring the plurality of projection images obtained by irradiating the subject disposed between the radiation source and the radiation detector with radiation emitted from the radiation source at different irradiation angles and capturing the radiation with the radiation detector at each of the irradiation angles;
generating a plurality of tomographic images reconstructed from the plurality of projection images;
in the plurality of tomographic images, performing a noise processing of reducing a weight of a noise pixel which is more affected by noise with respect to corresponding pixels on a specific projection path or excluding the noise pixel, wherein the specific projection path is a projection path through which a radiation image is projected by the radiation passing through a pixel of an object of interest, and
generating the pseudo two-dimensional image using the plurality of tomographic images reconstructed from the plurality of projection images after the noise processing.

11. A non-transitory recording medium storing an image processing program that causes a computer to perform:
acquiring a plurality of projection images obtained by irradiating a subject disposed between a radiation source and a radiation detector with radiation emitted from the radiation source at different irradiation angles and capturing the radiation with the radiation detector at each of the irradiation angles;
generating a plurality of tomographic images reconstructed from the plurality of projection images;
in the plurality of tomographic images, performing a noise processing of reducing a weight of a noise pixel which is more affected by noise with respect to corresponding pixels on a specific projection path or excluding the noise pixel, wherein the specific projection path is a projection path through which a radiation image is projected by the radiation passing through a pixel of an object of interest, and generating a pseudo two-dimensional image using a plurality of tomographic images reconstructed from the plurality of projection images after the noise processing.

12. An image processing apparatus comprising:
a processor configured to
acquire a plurality of projection images obtained by irradiating a subject disposed between a radiation source and a radiation detector with radiation emitted from the radiation source at different irradiation angles and capture the radiation with the radiation detector at each of the irradiation angles;
decompose each of the plurality of projection images into a plurality of first projection images with a low-frequency component lower than a predetermined spatial frequency and a plurality of second projection images with a high-frequency component higher than the predetermined spatial frequency;
generate a plurality of first tomographic images reconstructed from the plurality of first projection images weighted according to radiation angles;
generate a plurality of second tomographic images reconstructed from the plurality of second projection images;
in each of the plurality of second tomographic images that were generated, perform a noise processing of reducing a weight of a noise pixel which is more affected by noise with respect to corresponding pixels on a specific projection path excluding the noise pixel, wherein the specific projection path is a projection path through which a radiation image is projected by the radiation passing through a pixel of an object of interest; and
generate a pseudo two-dimensional image using the plurality of first tomographic images and the plurality of second tomographic images after the noise processing.

13. The image processing apparatus according to claim 12,
wherein, in a case in which a plurality of noise pixels are present on the projection path, the processor reduces the weights of some of the noise pixels or excludes some of the noise pixels.

14. The image processing apparatus according to claim 13,
wherein a ratio of a number of the some noise pixels of the plurality of noise pixels to a number of tomographic images is equal to or less than a predetermined value.

15. The image processing apparatus according to claim 12,
wherein the processor generates a first pseudo two-dimensional image using the plurality of first tomographic images, generates a second pseudo two-dimensional image using the plurality of second tomographic images, and combines the first pseudo two-dimensional image and the second pseudo two-dimensional image to generate a composite pseudo two-dimensional image as the pseudo two-dimensional image.

16. The image processing apparatus according to claim 12,
wherein the processor combines each of the plurality of first tomographic images and each of the plurality of second tomographic images for each height according to the height based on a detection surface of the radiation detector to generate a plurality of composite tomographic images and generates a composite pseudo two-dimensional image as the pseudo two-dimensional image, using the plurality of composite tomographic images.

17. An image processing method using the image processing apparatus according to claim 12 comprising:
acquiring the plurality of projection images obtained by irradiating the subject disposed between the radiation source and the radiation detector with radiation emitted from the radiation source at different irradiation angles and capturing the radiation with the radiation detector at each of the irradiation angles;
decomposing each of the plurality of projection images into a plurality of first projection images with a low-frequency component lower than a predetermined spatial frequency and a plurality of second projection images with a high-frequency component higher than the predetermined spatial frequency;
generating a plurality of first tomographic images reconstructed from the plurality of first projection images weighted according to radiation angles;
generating plurality of second tomographic images reconstructed from the plurality of second projection images;
in each of the plurality of second tomographic images that were generated, performing a noise processing of reducing a weight of a noise pixel which is more affected by noise with respect to corresponding pixels on a specific projection path passing through a pixel of an object of interest or excluding the noise pixel, wherein the specific projection path is a projection path through which a radiation image is projected by the radiation passing through a pixel of an object of interest; and
generating a pseudo two-dimensional image using the plurality of first tomographic images and the plurality of second tomographic images after the noise processing.

18. A non-transitory recording medium storing an image processing program that causes a computer to perform:
acquiring the plurality of projection images obtained by irradiating the subject disposed between the radiation source and the radiation detector with radiation emitted from the radiation source at different irradiation angles and capturing the radiation with the radiation detector at each of the irradiation angles;
decomposing each of the plurality of projection images into a plurality of first projection images with a low-frequency component lower than a predetermined spatial frequency and a plurality of second projection images with a high-frequency component higher than the predetermined spatial frequency;
generating a plurality of first tomographic images reconstructed from the plurality of first projection images weighted according to radiation angles;
generating plurality of second tomographic images reconstructed from the plurality of second projection images;
in each of the plurality of second tomographic images that were generated, performing a noise processing of reducing a weight of a noise pixel which is more affected by noise with respect to corresponding pixels on a specific projection path passing through a pixel of an object of interest or excluding the noise pixel, wherein the specific projection path is a projection path through which a radiation image is projected by the radiation passing through a pixel of an object of interest; and generating a pseudo two-dimensional image using the plurality of the first tomographic images and the plurality of the second tomographic images after the noise processing.

* * * * *